(12) United States Patent
Karthikeyan et al.

(10) Patent No.: US 11,136,581 B2
(45) Date of Patent: Oct. 5, 2021

(54) INHIBIN AS TARGETABLE REGULATORS OF ANGIOGENESIS

(71) Applicant: University of South Carolina, Columbia, SC (US)

(72) Inventors: Mythreye Karthikeyan, Columbia, SC (US); Priyanka Singh, Columbia, SC (US)

(73) Assignee: University of South Carolina, Aiken, SC (US)

( * ) Notice: Subject to any disclaimer, the term of this patent is extended or adjusted under 35 U.S.C. 154(b) by 0 days.

(21) Appl. No.: 15/631,561

(22) Filed: Jun. 23, 2017

(65) Prior Publication Data

US 2017/0369886 A1      Dec. 28, 2017

Related U.S. Application Data

(60) Provisional application No. 62/354,330, filed on Jun. 24, 2016, provisional application No. 62/372,902, filed on Aug. 10, 2016.

(51) Int. Cl.

| | |
|---|---|
| *G01N 33/53* | (2006.01) |
| *C12N 5/00* | (2006.01) |
| *C07K 14/00* | (2006.01) |
| *C07K 16/00* | (2006.01) |
| *C12N 15/113* | (2010.01) |
| *A61K 31/713* | (2006.01) |
| *A61K 45/06* | (2006.01) |
| *A61P 35/00* | (2006.01) |

(52) U.S. Cl.
CPC ........ *C12N 15/1136* (2013.01); *A61K 31/713* (2013.01); *A61K 45/06* (2013.01); *A61P 35/00* (2018.01); *C12N 2310/14* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 5,928,641 A | 7/1999 | Seon | |
| 2009/0068690 A1* | 3/2009 | Fischer | G01N 33/57449 435/7.92 |
| 2009/0226441 A1* | 9/2009 | Yan | A61K 39/39558 424/134.1 |
| 2009/0252735 A1* | 10/2009 | Milne-Robertson | A61P 5/00 424/139.1 |
| 2011/0076263 A1* | 3/2011 | Theuer | C07K 16/2896 424/130.1 |
| 2011/0110944 A1 | 5/2011 | Steidl et al. | |
| 2013/0089869 A1 | 4/2013 | Blobe et al. | |

FOREIGN PATENT DOCUMENTS

| | | | |
|---|---|---|---|
| WO | WO-0129079 A1 * | 4/2001 | ........... C07K 14/575 |
| WO | WO2015/186128 | 12/2015 | |

OTHER PUBLICATIONS

Liu et al. Studies on enhancing embryo quantity and quality by immunization against inhibin in repeatedly superovulated Holstein heifers and the associated endocrine mechanisms. Animal Reproduction Science 142:10-18 (2013). (Year: 2013).*
Rivier et al. Inhibin-Mediated Feedback Control of Follicle-Stimulating Hormone Secretion in the Female Rat. Science 234 (4773), 205-208 (Oct. 1986). (Year: 1986).*
Bhattacharya et al. Impact of genetic variation on three dimensional structure and function of proteins; PLOS One 12(3): e0171355, pp. 1-22 (Mar. 2017) (Year: 2017).*
Tokuriki et al., Stability effects of mutations and protein evolvability; Current Opinion in Structural Biology, 19:596-604 (2009). (Year: 2009).*
Lloyd et al. Modelling the human immune response: performanceof a 1011 human antibody repertoire against a broad panel of therapeutically relevant antigens. Protein Engineering, Design & Selection vol. 22/No. 3:159-168 (2009). (Year: 2009).*
Doi et al. A phase I study of the human anti-activin receptor-like kinase 1 antibody PF-03446962 in Asian patients with advanced solid tumors. Cancer Medicine vol. 5(7): 1454-1463 (Jul. 2016). (Year: 2016).*
El-Shalakany et al. Preoperative serum inhibin levels in patients with ovarian tumors. Journal Obstet. Gynaecol. Research vol. 30, No. 2: 155-161 (Apr. 2004). (Year: 2004).*
Ahmed et al. Getting to know ovarian cancer ascites: opportunities for targeted therapy-based translational research. Frontiers in Oncology 2013;3:256.
Balanathan et al. Elevated level of inhibin-α subunit is pro-tumourigenic and pro-metastatic and associated with extracapsular spread in advanced prostate cancer. British Journal of Cancer 2009;100:1784-93.
Barbara et al. Endoglin is an accessory protein that interacts with the signaling receptor complex of multiple members of the transforming growth factor-β superfamily. Journal of Biological Chemistry 1999; 274:584-94.
Bertolino et al. Transforming growth factor-β signal transduction in angiogenesis and vascular disorders. Chest 2005;128:585S-90S.

(Continued)

*Primary Examiner* — Elizabeth C. Kemmerer
*Assistant Examiner* — Regina M DeBerry
(74) *Attorney, Agent, or Firm* — Dority & Manning, P.A.

(57) ABSTRACT

Contact of endothelial cells with inhibitors of inhibin and/or the alpha subunit of inhibin can be utilized to modify the activity of endothelial cell expression products including SMAD 1/5. Methods can also include inhibiting Alk1 and/or endoglin as components of inhibin-activated pathway of SMAD 1/5 signaling. Methods can be combined with other anti-angiogenesis therapies such as anti-VEGF therapies. Methods can be utilized in treatment of inhibin-expressing cancers (e.g., ovarian cancer, pancreatic cancer) as well as other pathologies such as preeclampsia and PCOS.

7 Claims, 23 Drawing Sheets

(56) References Cited

OTHER PUBLICATIONS

Cai et al. Molecular Mechanisms of Enhancing Porcine Granulosa Cell Proliferation and Function by Treatment In Vitro with Anti-Inhibin Alpha Subunit Antibody, Reproductive Biology and Endocrinology, 2015, 13-26, 1-10.
Connolly et al. Xenograft and transgenic mouse models of epithelial ovarian cancer and non-invasive imaging modalities to monitor ovarian tumor growth in situ: applications in evaluating novel therapeutic agents. Current Protocols in Pharmacology I Editorial board, SJ Enna 2009;Chapter 14:Unit14 2.
David et al. Emerging role of bone morphogenetic proteins m angiogenesis. Cytokine Growth & Factor Review 2009;20:203-12.
David et al. Identification of BMP9 and BMP10 as functional activators of the orphan activin receptor-like kinase 1 (ALK1) in endothelial cells. Blood 2007;109:1953-61.
Deccicco-Skinner et al. Endothelial cell tube formation assay for the in vitro study of angiogenesis. Journal of Visualized Experiments 2014:e51312.
Farnworth et al, Inhibin binding sites and proteins in pituitary, gonadal, adrenal and bone cells. Molecular and Cellular Endocrinology 2001;180:63-71.
Gatza et al. Roles for the type III TGF-β receptor in human cancer. Cell Signaling 2010;22:1163-74.
Gilboa et al. Bone morphogenetic protein receptor complexes on the surface of live cells: a new oligomerization mode for serine/threonine kinase receptors. Molecular Biology of the Cell 2000;11:1023-35.
Gilboa et al. Oligomeric structure of type I and type II transforming growth factor β receptors: homodimers form in the ER and persist at the plasma membrane. Journal of Cell Biology 1998; 140:767-77.
Goumans et al. Activin receptor-like kinase (ALK)1 is an antagonistic mediator of lateral TGFβ/ALK5 signaling. Molecular Cell 2003;12:817-28.
Inman et al. SB-431542 is a potent and specific inhibitor of transforming growth factor-β superfamily type I activin receptor-like kinase (ALK) receptors ALK4, ALK5, and ALK7. Molecular Pharmacology 2002;62:65-74.
Jazaeri et al. Molecular requirements for transformation of fallopian tube epithelial cells into serous carcinoma. Neoplasia 2011;13:899-911.
Jin et al. VEGF, Notch and TGFβ/BMPs in regulation of sprouting angiogenesis and vascular patterning. Biochemical Society Transactions 2014;42: 1576-83.
Jonker. TGF-β & BMP receptors endoglin and ALK1: overview of their functional role and status as antiangiogenic targets. Microcirculation 2014;21:93-103.
Kaivo-Oja et al., Smad Signaling in the Ovary, Reproductive Biology and Endocrinology, 2006; 4-21, 1-13.
Kaneda et al. Activin A inhibits vascular endothelial cell growth and suppresses tumour angiogenesis in gastric cancer. British Journal of Cancer 2011;105:1210-7.
Kumar et al. Antibody directed coupling of endoglin and MMP-14 is a key mechanism for endoglin shedding and deregulation of TGF-β signaling. Oncogene 2014;33:3970-9.
Laib et al. Spheroid-based human endothelial cell microvessel formation in vivo. Nature protocols 2009;4:1202-15.
Lewis et al., Betaglycan Binds Inhibin and can Mediate Functional Antagonism of Activin Signaling, Nature, 2000, 404-6776, 411-414.
Looyenga et al. Inhibin-A antagonizes TGF-β signaling by down-regulating cell surface expression of the TGFβ coreceptor betaglycan. Molecular Endocrinology 2010;24:608-20.
Malinda. In vivo matrigel migration and angiogenesis assay. Methods in Molecular Biology 2009;467:287-94.
Massague et al. The TGF-β family and its composite receptors. Trends in Cell Biology 1994:4:172-8.
Matzuk et al, α-inhibin is a tumour suppressor gene with gonadal specificity in mice. Nature 1992;360:313-9.

McCluggage et al. Immunohistochemical staining of hepatocellular carcinoma with monoclonal antibody against inhibin. Histopathology 1997;30:518-22.
McCluggage et al. Adenocarcinomas of various sites may exhibit immunoreactivity with anti-inhibin antibodies. Histopathology 1999;35:216-20.
Nassiri et al. Endoglin (CD105): a review of its role in angiogenesis and tumor diagnosis, progression and therapy. Anticancer Research 2011;31:2283-90.
Overlie et al. Inhibit A and B as markers of menopause: a five-year prospective longitudinal study of hormonal changes during the menopausal transition. Acta Obstetricia et Gynecologica Scandinavica 2005;84:281-5.
Pardali et al. Transforming growth factor-beta signaling and tumor angiogenesis. Frontiers in Bioscience (Landmark Ed) 2009;14:4848-61.
Pece-Barbara et al. Endoglin null endothelial cells proliferate faster and are more responsive to transforming growth factor β1 with higher affinity receptors and an activated Alk1 pathway. Journal of Biological Chemistry 2005;280:27800-8.
Pecot et al. Tumour angiogenesis regulation by the miR-200 family, Nature Communications 2013;4:2427.
Pomeraniec et al. Regulation of TGF-β receptor hetero-oligomerization and signaling by endoglin. Molecular Biology of the Cell 2015;26:3117-27.
Robertson et al. Inhibin as a diagnostic marker for ovarian cancer. Cancer Letters 2007;249:14-7.
Rosen et al. A Phase 1 First-in-Human Study of TRC105 (Anti-Endoglin Antibody) in Patients with Advanced Cancer. Clinical Cancer Research 2012;18:4820-9.
Shanbhag et al. Immunoreactive inhibin-like material in serum and gastric juice of patients with benign and malignant diseases of the stomach, British Journal of Cancer 1985. 51:877-82.
Shaw et al. Characterization of intraperitoneal, orthotopic, and metastatic xenograft models of human ovarian cancer. Molecular Therapy: The Journal of the American Society of Gene Therapy 2004;10:1032-42.
Söderberg et al. Direct observation of individual endogenous protein complexes in situ by proximity ligation. Nature Methods 2006;3:995-1000.
Stone et al. Focal adhesion kinase: an alternative focus for anti-angiogenesis therapy in ovarian cancer. Cancer Biology & Therapy 2014;15:919-29.
Suzuki et al, Immunohistochemical similarities between pancreatic mucinous cystic tumor and ovarian mucinous cystic tumor. Pancreas 2008;36:e40-6.
Tan et al. Mechanisms of transcoelomic metastasis in ovarian cancer. The Lancet Oncology 2006;7:925-34.
Tian et al. Endoglin mediates fibronectin/α5β1 integrin and TGF-β pathway crosstalk in endothelial cells. The EMBO journal 2012;31:3885-900.
Varadaraj et al. TGF-β triggers rapid fibrillogenesis via a novel TβRII-dependent fibronectin-trafficking, mechanism. Molecular Biology of the Cell 2017.
Walentowicz et al. Serum inhibin A and inhibin B levels in epithelial ovarian cancer patients. PLoS One 2014;9:e90575.
Walton et al. The synthesis and secretion of inhibins. Vitamins and Hormones 2011;85:149-84.
Wang et al. Activin inhibits basal and androgen-stimulated proliferation and induces apoptosis in the human prostatic cancer cell line, LNCaP. Endocrinology 1996;137:5476-83.
Wiater et al., Inhibin is an Antagonist of Bone Morphogenetic Protein Signaling, Journal of Biological Chemistry, 2002, 278-10, 7934-7941.
Wu et al. A miR-192-EGR1-HOXB9 regulatory network controls the angiogenic switch in cancer, Nature Communications 2016;7:11169.
International Search Report for PCT/US2017/39076, dated Sep. 25, 2017.

* cited by examiner

INHIBIN AS TARGETABLE REGULATORS OF ANGIOGENESIS

CROSS REFERENCE TO RELATED APPLICATIONS

This application claims filing benefit of U.S. Provisional Patent Application Ser. No. 62/354,330 having a filing date of Jun. 24, 2016 entitled "Inhibins as Novel and Targetable Regulators of Angiogenesis," and U.S. Provisional Patent Application Ser. No. 62/372,902 having a filing date of Aug. 10, 2016, entitled, "Targeting Inhibins in Cancers and other Vascular Malignancies," both of which are incorporated herein by reference.

STATEMENT REGARDING FEDERALLY SPONSORED RESEARCH OR DEVELOPMENT

This invention was made with government support under grant no. 5P20GM109091-02 awarded by the National Institutes of Health. The government has certain rights in the invention.

BACKGROUND

Inhibins are heterodimeric molecules that are principally produced in the ovary by granulosa cells. Inhibins include an α subunit linked through disulfide binding with either a $β_A$ or $β_B$ subunit. The resulting $αβ_A$ heterodimer is referred to as inhibin A, whereas the $αβ_B$ protein constitutes inhibin B. Inhibin A is the predominant form produced during the late follicular and luteal phases of the normal menstrual cycle, whereas Inhibin B is the predominant form during the early and mid-follicular phases of the cycle. Inhibins are an endocrine hormone in the TGF-β family and selectively inhibit follicle-stimulating hormone (FSH) secretion by the pituitary. Inhibin has also been identified as an antagonist of activin, another TGF-β member.

Inhibin levels have been found to be significantly elevated across several ovarian cancer subtypes including GCT's, mucinous, clear cell, and high grade serous and also in the stroma of Brenner cancers associated with ascites accumulation such as colon, gastric, and pancreatic cancers (see, e.g., FIG. 1). Increased inhibin expression has also been reported in other vascular malignancies such as preeclampsia and polycystic ovary syndrome (PCOS). While the overexpression of inhibins has been noted in these and other pathologies, the functional role of the protein in disease has not been reported. During normal, non-pathogenic activity, inhibin binds the TGF-β receptor complex TβRIII (also known as betaglycan) expressed on epithelial cells to mediate functional antagonism of activin, and this is the only high affinity receptor molecule that has been shown to directly bind inhibin. However, TβRIII expression is greatly decreased in cancer (FIG. 2). Thus, the possible functional consequences of elevated inhibin in cancers and other vascular malignancies remains elusive.

Angiogenesis refers to capillary formation from existing blood vessels. Angiogenesis occurs in several stages and involves interactions between cells, soluble factors, and extracellular matrix (ECM) molecules. First, endothelial cells with the help of proteolytic enzymes, including matrix metalloproteases (MMPs) break down the basement membrane of an existing blood vessel and invade the surrounding tissues. After the basement membrane of the blood vessel is broken down, endothelial cells migrate into the surrounding tissue and proliferate and sprout to give rise to new vessels. Growth factors and other soluble proteins often facilitate and regulate this process. Certain growth factors, such as vascular endothelial growth factor (VEGF), act as chemoattractants that facilitate the migration of endothelial cells to certain locations. After migration and proliferation, the endothelial cells form a new lumen and start to secrete ECM molecules, ultimately forming a new capillary.

Angiogenesis plays an important role in many normal events in the body, including wound healing, embryogenesis, and female reproductive processes. During these normal processes, angiogenesis is highly regulated. Unregulated angiogenesis however, contributes to many pathological processes, including many cancers and pathologies involving the reproductive system such as preeclampsia and PCOS.

What is needed in the art is a better understanding of the growth factors such as inhibin produced under pathological conditions and their role in angiogenesis and methods for utilizing that understanding.

SUMMARY

According to one embodiment, disclosed is a method for preventing pathological angiogenesis through inhibition of inhibin and, in one particular embodiment, through inhibition of the alpha subunit of inhibin. More specifically, a method can inhibit expression or signaling of SMAD1 and/or SMAD 5 as well as other pathways in endothelial cells through contact of the cells with a composition that includes an agent configured to inhibit the presence or activity inhibin. The agent can be directed at the isolated alpha subunit or optionally at complete inhibin, either inhibin A or inhibin B.

According to one embodiment, a method can include inhibiting the presence or functional activity of inhibin in conjunction with inhibiting one or more components of a receptor utilized in pathological activity of inhibin. For instance, a method can include contacting endothelial cells with a composition that includes an agent configured to inhibit the presence or activity of inhibin (e.g., the alpha subunit of inhibin) and also includes an agent configured to inhibit the presence or activity of activin receptor-like kinase 1 (Alk1) and/or an agent configured to inhibit the presence or activity of endoglin.

A composition is also disclosed for carrying out disclosed methods. For instance, a composition can include a biologically acceptable carrier in conjunction with an agent configured to inhibit the presence or activity of inhibin and can also include an agent configured to inhibit the presence or activity of Alk1 and/or an agent configured to inhibit the presence or activity of endoglin. The active agents of a composition can include antibodies, interfering RNA (e.g., shRNA), small molecule inhibitors, soluble binding partners for binding fragments thereof (e.g., soluble TβRIII), etc.

BRIEF DESCRIPTION OF THE DRAWINGS

A full and enabling disclosure of the present invention, including the best mode thereof, directed to one of ordinary skill in the art, is set forth in the specification, which makes reference to the appended figure, in which.

DETAILED DESCRIPTION

Figure 1:
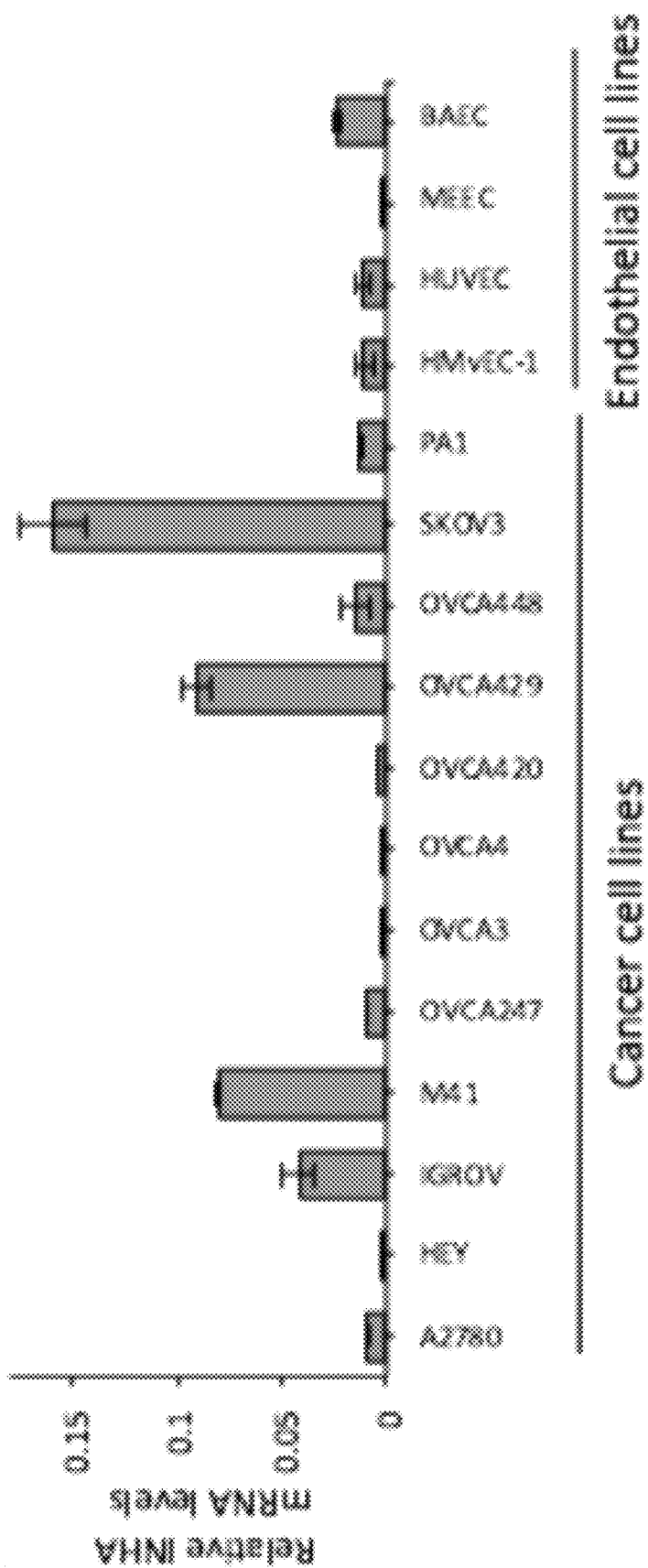
FIG. 1 compares the basal expression of the alpha chain of inhibin in several ovarian cancer cell lines and endothelial cells.
Figure 2:
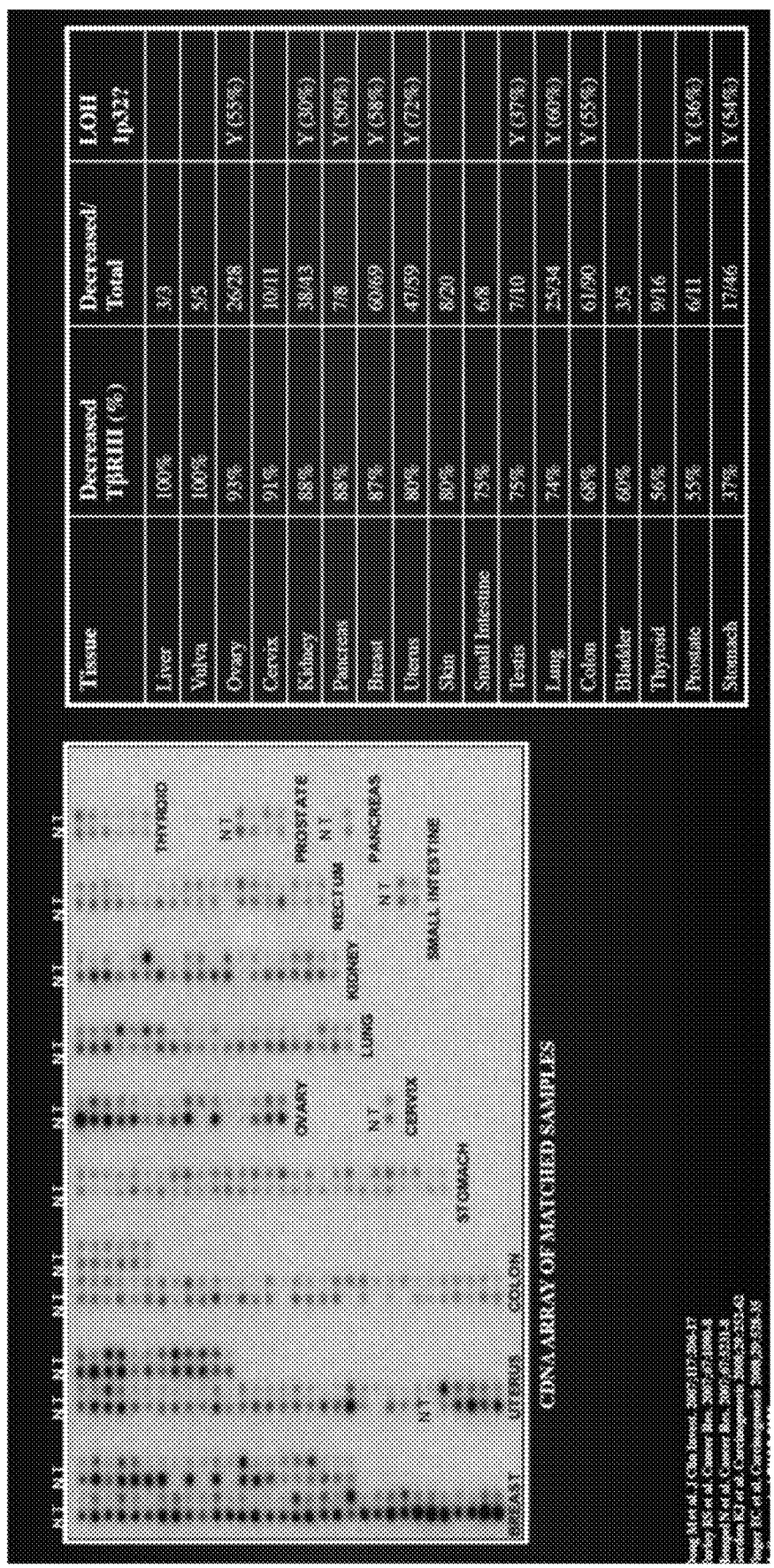
FIG. 2 demonstrates the decreased expression of the Type III TGFβ receptor (TβRIII) in cancer.

The following description and other modifications and variations to the present invention may be practiced by those of ordinary skill in the art, without departing from the spirit and scope of the present invention. In addition, it should be understood that aspects of the various embodiments may be interchanged in whole and in part. Furthermore, those of ordinary skill in the art will appreciate that the following description is by way of example only, and is not intended to limit the invention.

In general, disclosed herein is are methods and materials for modifying the activity of certain endothelial cell expression products, and in particular, expression products involved in angiogenesis. More specifically, the disclosure is directed to methods for modifying endothelial cell activity through control of the presence or functional activity (and in particular paracrine-type activity) of inhibin in an environment that includes the endothelial cells.

In one embodiment, disclosed methods and materials can directly target inhibin presence or functional activity in an environment that includes endothelial cells through utilization of an agent such as, and without limitation to, an antibody (or functional fragment thereof), a small molecule inhibitor, RNAi, or a soluble binding partner or fragment thereof, directed at inhibin, and in one particular embodiment directed at the α subunit of inhibin. Inhibition of inhibin in the environment can affect the activity and/or expression of endothelial cell components involved in pathological angiogenesis. For instance, inhibition of inhibin can decrease SMAD 1 and/or SMAD 5 signaling in endothelial cells, which is a necessary component of angiogenesis. Other pathways can likewise be affected through the disclosed methods and materials. For instance, targeting of inhibin can affect the mitogen-activated protein kinase (MAPK) cascades, which have been shown to play a key role in transduction of extracellular signal to cellular response and play an important role in cellular programs such as proliferation, differenti9ation, development, transformation, and apoptosis.

In another embodiment, methods can indirectly target the angiogenesis-promoting activity of inhibin. In this embodiment, methods and materials can target components of a receptor complex signaling pathway including Alk1 and/or endoglin. As described further herein, this receptor complex has been discovered to be an alternate endothelial receptor complement system to the TβRIII receptor complex that is often lost in cancer. These co-receptors are elevated in the ascites of certain cancer patients (e.g., ovarian cancer patients) and have been discovered to be mediators in inhibin signaling and inhibin-induced angiogenesis in endothelial cells. In this embodiment, a method can include inhibition of the presence or activity of one or both of these components of the alternate signaling pathway in conjunction with direct targeting of inhibin so as to modify the activity of certain angiogenesis-related compounds in endothelial cells, for instance in order to modify activity of one or more of the SMAD1/5 pathway or one or more MAPK pathways such as ERK 1/2 signaling that, in vivo, can affect angiogenesis.

Disclosed materials can be utilized in vivo in preventing pathological angiogenesis. For instance, the methods and materials can be utilized to decrease the presence and/or activity of inhibin in disorders in which dysregulation in angiogenesis contributes to the pathology, and particularly in those disorders in which inhibin expression is also significantly elevated. Examples of such pathologies can include, without limitation to, certain cancers (e.g., ovarian cancer, prostate cancer, renal langer, lung cancer, gastric cancer, and breast cancer) as well as other diseases that include vascular malignancies such as preeclampsia and PCOS.

As discussed further herein, the methods and materials are based upon the recognition that the α-subunit of inhibin (also referred to as inhibinα and α-inhibin throughout this disclosure), critical for the functionality of dimeric inhibin (both A and B), is produced in a broad spectrum of tumors and this production correlates with microvessel density (MVD) in human ovarian tissues and xenografts and is also predictive of poor clinical outcomes in multiple cancers. Notably, both cancer cell-derived and recombinant inhibin is shown herein to elicit a strong paracrine response from endothelial cells by triggering SMAD1/5 activation and angiogenesis both in vitro and in vivo.

In addition, it has been discovered that inhibin is an alternate ligand for endoglin (ENG; also commonly referred to as CD105) and induces SMAD 1/5 expression through an Alk1/ACTRII pathway. As such, pathological angiogenesis prevention can also include inhibition of one or more components of this pathway, and in one embodiment, via inhibition of endoglin and/or Alk1.

Figure 3:
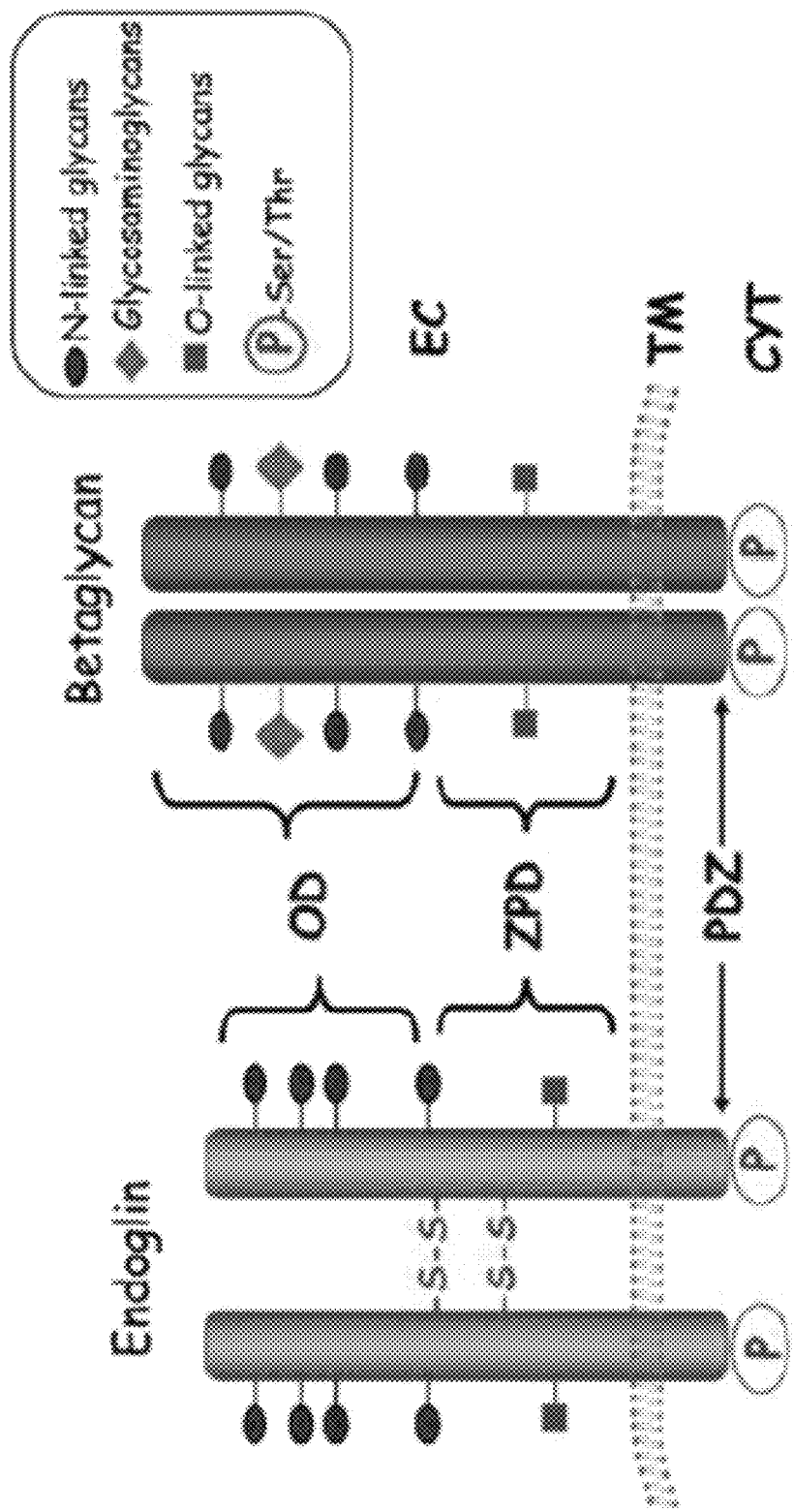
FIG. 3 is a comparison between endoglin and TβRIII.

FIG. 3 provides a comparison between endoglin and betaglycan (TβRIII), the widely known TGF-β receptor complex that binds inhibin. While superficially similar, as shown in FIG. 3, the activity of betaglycan and endoglin in pathology appears to be quite different. For instance, betaglycan is known to be downregulated in multiple tumor types, including neuroblastoma, ovarian granulosa, ovarian carcinoma, endometrial carcinoma, prostate carcinoma, breast carcinoma, renal cell carcinoma, non-small cell lung cancer, and pancreatic carcinoma. Endoglin, in contrast, has high serum levels in several pathologies including breast carcinoma variants, colorectal carcinoma, acute myeloid leukemia, and chronic myeloid leukemia. It is overexpressed in breast carcinoma variants and subject to germline mutation in juvenile polyposis. It is downregulated in prostate carcinoma and esophageal squamous carcinoma, but presents high plasma levels in prostate carcinoma. (Bernabeu, et al., *BBA*, 2009)

Endoglin has previously been associated with angiogenesis. For instance, endoglin expression levels in the vasculature are increased during angiogenesis, with a decreased expression leading to altered angiogenesis in vitro and aberrant vascular development and function in vivo. Mutations in a single allele of the endoglin gene can result in decreased level of the protein and are associated with hereditary hemorrhagic telangiectasia-1 (HHT-1) and vascular malformations in humans. Moreover, endoglin deficient (Eng-/-) mice have been shown to succumb to cardiovascular defects due to inappropriate remodeling of mature vascular network. (Bernabeu, et al., *BBA*, 2009).

Figure 4:
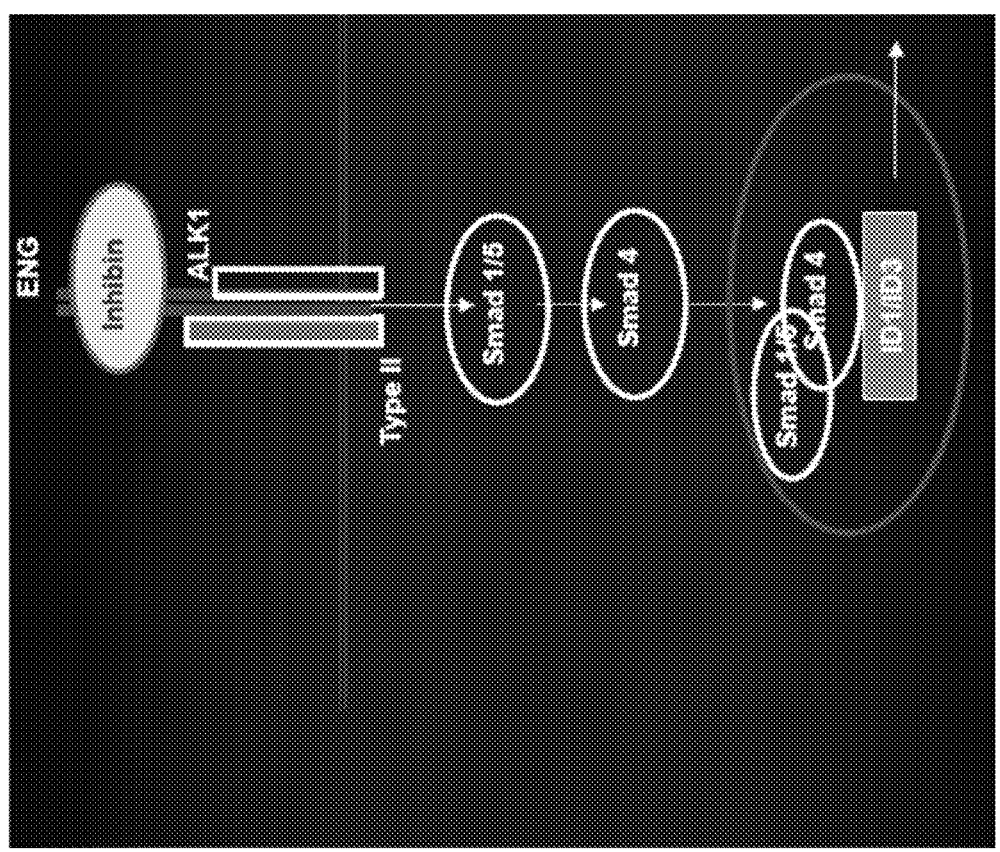
FIG. 4 schematically illustrates the interaction of inhibin, endoglin, Alk1, and ACTRII in activation of the SMAD 1/5 pathway.
Figure 5:
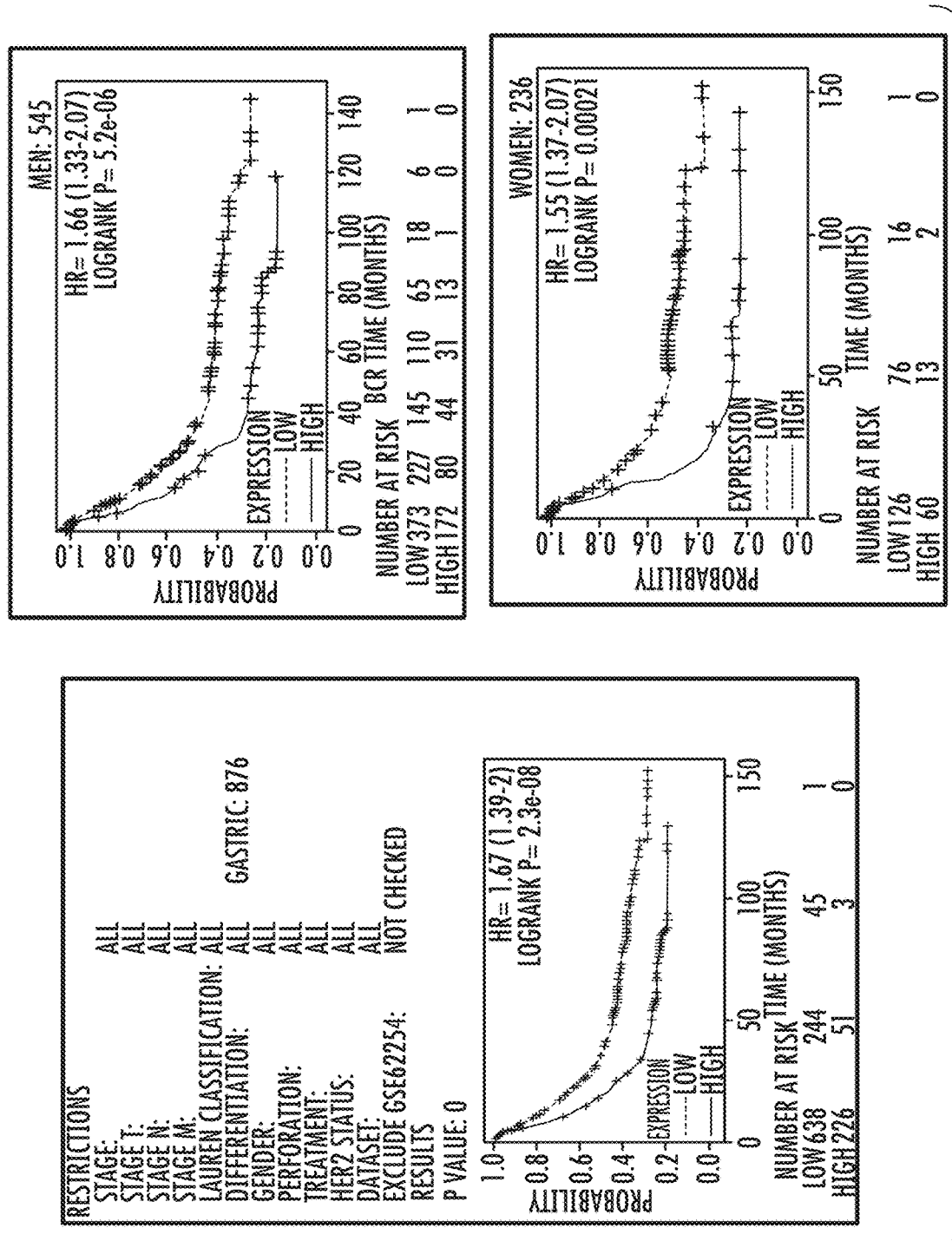
FIG. 5 demonstrates inhibin as a predictor of patient survival in gastric cancer.
Figure 6:
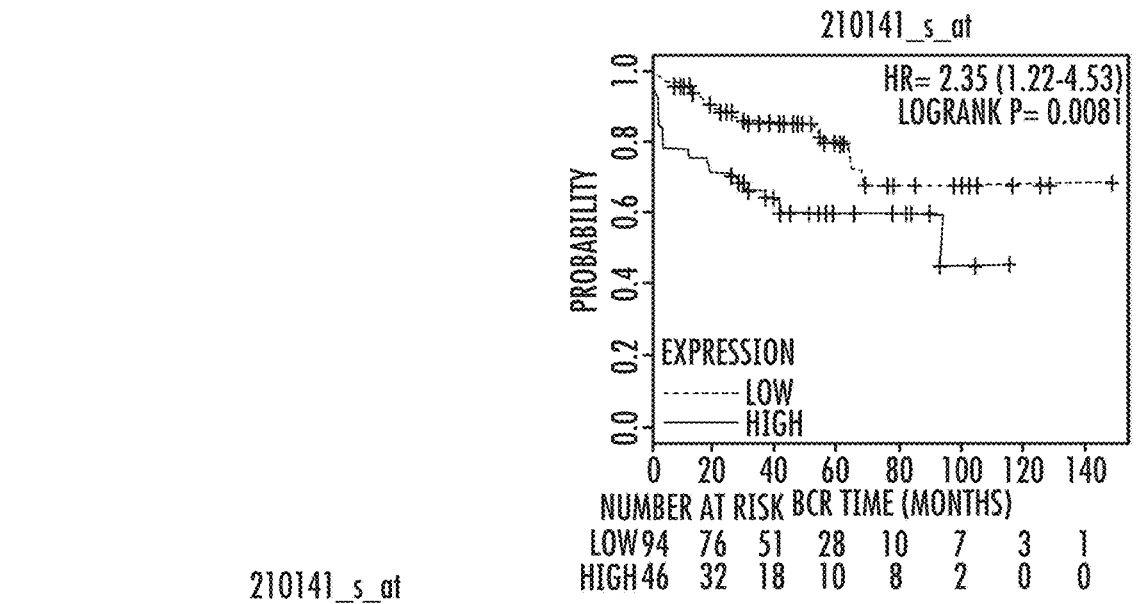
FIG. 6 demonstrates inhibin as a predictor of patient survival in prostate cancer.
Figure 7:
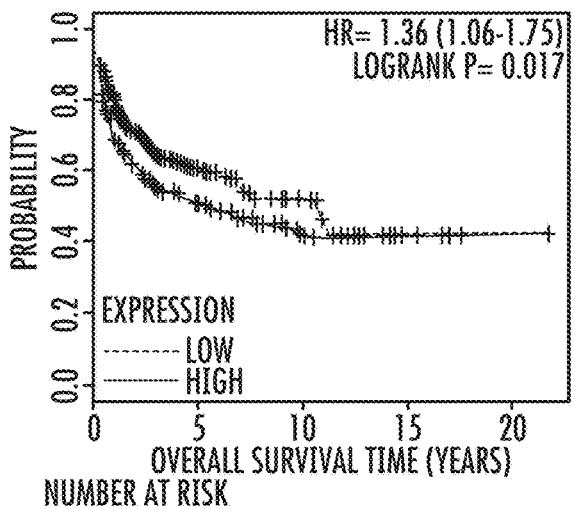
FIG. 7 demonstrates inhibin as a predictor of patient survival in diffuse large cell B cell lymphoma.
Figure 8:
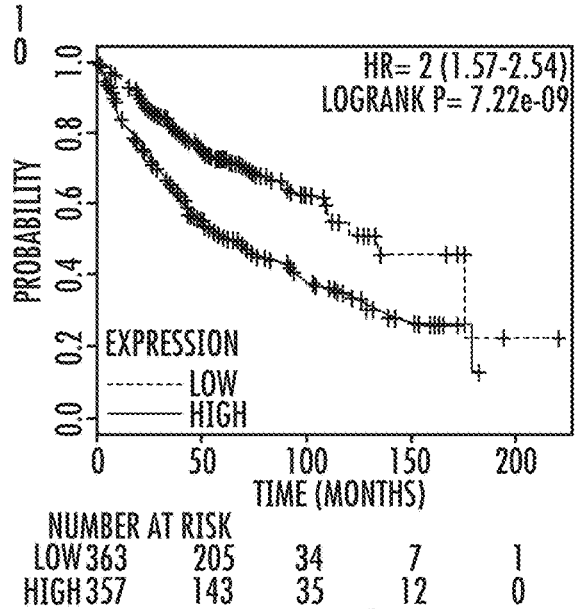
FIG. 8 demonstrates inhibin as a predictor of patient survival in lung adenocarcinoma.
Figure 9:
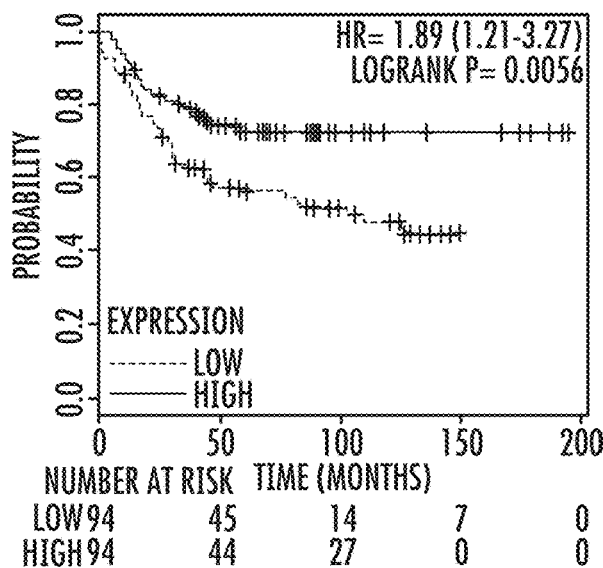
FIG. 9 demonstrates inhibin as a predictor of patient survival in p53 mutated breast cancer.
Figure 10:
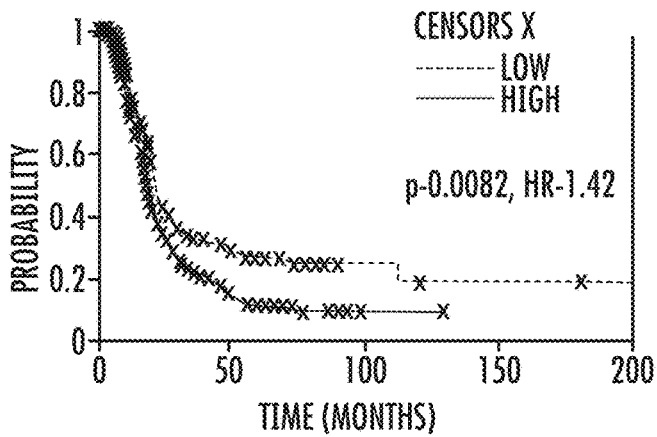
FIG. 10 demonstrates inhibin as a predictor of patient survival in ovarian cancer.
Figure 11:
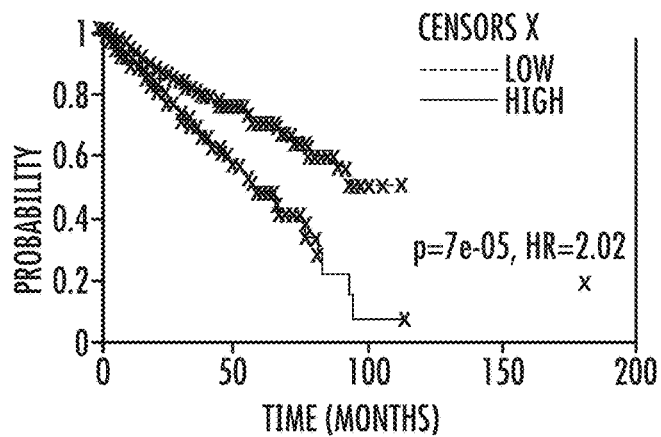
FIG. 11 demonstrates inhibin as a predictor of patient survival in renal clear cell cancer.

The presently disclosed methods and materials have been developed based upon the discovery of interaction between inhibin and endoglin in pathological angiogenesis. Without wishing to be bound to any particular theory, and as schematically illustrated in FIG. 4, it is believed that increased expression of inhibin, and in particular the alpha subunit of inhibin in certain pathologies (e.g., ovarian and prostate cancers), provides a route for pathological angiogenesis through interaction with endoglin via the Alk1/ACTRII pathway and activation of SMAD 1/5, as shown. As such, inhibition of pathologically expressed inhibin, optionally in conjunction with inhibition of one or more of endoglin and Alk1, can serve to prevent expression/activation of SMAD 1/5 and subsequent angiogenesis.

As utilized herein, the term "inhibition" is intended to refer to prevention of expression of the target as well as to inactivation of the expressed target. For example, inhibition agents for use in preventing the presence and/or activity of a target (e.g., inhibin, α-inhibin, endoglin, Alk1, or combinations thereof) can include antibodies, RNAi, small molecule inhibitors, ligand traps (i.e., soluble binding partners of the target), and the like.

An inhibition agent configured to prevent activity of a target can be a polypeptide, e.g., either a complete protein or a fragment thereof, that can recognize and bind the target or alternatively can be a non-proteinaceous binding agent. For instance, an inhibition agent can be an antibody (e.g., an anti-α-inhibin antibody) or a soluble proteinaceous binding partner of the target (e.g., soluble betaglycan), also referred to as a ligand trap. Non-proteinaceous binding agents can include small molecule inhibitors as are available in the art.

Anti-inhibin and anti-α-inhibin antibodies as may be utilized are known and are available from suppliers such as Santa Cruz Biotechnology, Inc., Bio-Rad Antibodies, Novus Biologicals, and others. Antibodies can include polyclonal or monoclonal antibodies as desired. Antibodies can be raised according to known methods. For instance, isolated and/or purified or recombinantly produced inhibin or the isolated alpha subunit of inhibin may be utilized to generate antibodies using the methods known in the art. Humanized antibody to Alk1 and endoglin are likewise available in the open market. For instance, a humanized antibody to endoglin known as TRCN105 is in clinical trials and other endoglin antibodies have been described (see, e.g., U.S. Pat. No. 5,928,641, and US Patent Application Publication No. 2011/0110944, which are incorporated herein by reference).

In one embodiment, expression of inhibin, and in one particular embodiment, the alpha subunit of inhibin, can be prevented by silencing methods as are known in the art. For example, RNAi, e.g., shRNA-mediated knockdown, can be utilized to prevent expression of the target and thereby prevent endothelial cell signaling that can lead to pathological angiogenesis. A variety of sources for developing or purchasing RNAi materials for specific targeting are available to those of skill in the art.

Non-proteinaceous small molecule inhibitors can also be utilized that can bind the target and thereby prevent pathogenic angiogenesis in vivo. For instance, MLK347 is a highly selective Alk1/Alk2 small molecule inhibitor available from MCE® MedChem Express.

In general, an inhibition agent (or combination thereof) can be provided as a biocompatible composition. A composition can generally include the agent in a concentration that can vary over a wide range, with a preferred concentration generally depending on the particular application, the delivery site and the mode that will be used in the delivery process. For example, a composition can include an inhibition agent (e.g., an anti-α-antibody) at a concentration of from about 0.0001 µM to about 0.5 M, or from about 0.0001 µM to about 0.1 M so as to contact an endothelial cell at a concentration of between about 0.001 µM and about 100 µM. It should be noted, however, that while these exemplary concentrations are effective in certain embodiments, the composition can include a wider range of concentrations. For example, actual concentrations used may be influenced by the tissue targeted by the procedure, size of the targeted area, desired incubation time, and preferred pH, in addition to delivery mode.

In one embodiment, an inhibition agent can be provided in pharmaceutically acceptable formulations using formulation methods known to those of ordinary skill in the art. These formulations can generally be targeted to endothelial cells by standard routes. For example, the formulations may be administered in one embodiment directly to endothelium and/or to a tumor associated with the endothelium, for instance through exposure of the tissue and direct application thereto, or via direct injection of the formulation to the targeted tissue. In other embodiments, however, the formulations may be administered indirectly to the targeted tissue, e.g., via systemic administration.

The composition can be delivered intravenously in a systemic delivery protocol. For example, osmotic minipumps may be used to provide controlled delivery of high concentrations of the treatment agents through cannulae to the site of interest, such as directly into a tumor.

A composition can include additional agents, in addition to the inhibition agent. Such agents can be active agents, providing direct benefit to the tissue, or may be supporting agents, improving delivery, compatibility, or reactivity of other agents in the composition.

In one embodiment, disclosed methods can be utilized in conjunction with other anti-angiogenic methods and materials. For instance, and as discussed in more detail below, the inhibin-mediated pathway described herein can synergize in disease conditions with VEGF to stimulate endothelial cell differentiation and angiogenesis. Accordingly, in one embodiment, disclosed methods and materials can be utilized in conjunction with anti-VEGF therapies as are known in the art to provide even better treatment outcomes.

A composition can include one or more buffers as are generally known in the art. For example, a composition including an anti-α-inhibin antibody optionally in conjunction with an inhibition agent directed at endoglin and/or an inhibition agent directed at Alk1, and having a pH from about 4.0 to about 9.0 may be formulated with inclusion of a biocompatible buffer such as distilled water, saline, phosphate buffers, borate buffers, HEPES, PIPES, and MOPSO. In one embodiment, a composition may be formulated to have a pH of between about 5.5 and about 7.4.

Compositions for parenteral delivery, e.g., via injection, can include pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, the composition can contain minor amounts of auxiliary substances such as wetting or emulsifying agents, pH buffering agents and the like that can enhance the effectiveness of the phenolic compound. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents.

Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

In one embodiment, the compositions can include pharmaceutically acceptable salts of the components therein, e.g., those that may be derived from inorganic or organic acids. Pharmaceutically acceptable salts include the acid addition salts that are formed with inorganic acids such as, for example, hydrochloric or phosphoric acids, or such organic acids as acetic, tartaric, mandelic and the like. Salts formed with free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

In one embodiment the method can include use of timed release or sustained release delivery systems as are generally known in the art. Such systems can be desirable, for instance, in situations where long term delivery of the agents to a particular location is desired. According to this particular embodiment, a sustained-release matrix can include a matrix made of materials, usually polymers, which are degradable by enzymatic or acid/base hydrolysis or by dissolution. Once located at or near the target tissue, e.g., inserted into the body, for instance in the form of a patch or a stent, such a matrix can be acted upon by enzymes and body fluids. The sustained-release matrix can be chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone.

In one embodiment, the inhibition agent can be targeted by use of a hydrogel delivery vehicle. Hydrogels include polymeric matrices that can be highly hydrated while maintaining structural stability. Suitable hydrogel matrices can include un-crosslinked and crosslinked hydrogels. In addition, crosslinked hydrogel delivery vehicles of the invention can optionally include hydrolyzable portions, such that the matrix can be degradable when utilized in an aqueous environment, e.g., in vivo. For example, the delivery vehicle can include a cross-linked hydrogel including a hydrolyzable cross-linking agent, such as polylactic acid, and can be degradable in vivo.

Hydrogel delivery vehicles can include natural polymers such as glycosaminoglycans, polysaccharides, proteins, and the like, as well as synthetic polymers, as are generally known in the art. A non-limiting list of hydrophilic polymeric materials that can be utilized in forming hydrogels can include dextran, hyaluronic acid, chitin, heparin, collagen, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like.

A delivery system can include a combination of one or more delivery vehicles. For instance, a hydrogel delivery vehicle can be combined with a patch, a stent, a perforated balloon, a vascular graft, or any other suitable device, for delivery of the inhibition agent(s) to a target.

As discussed above, reports have detailed elevated inhibin in ovarian and prostate cancers and other studies have observed elevated in other cancers, such as colon cancer. In addition, inhibin can be a significant predictor of patient survival in cancers as illustrated in FIG. 5-11 for gastric cancer (FIG. 5), prostate cancer (FIG. 6), diffuse large cell B cell lymphoma (FIG. 7), lung adenocarcinoma (FIG. 8), and p53 mutated breast cancer (FIG. 9), ovarian cancer (FIG. 10), renal clear cell cancer (FIG. 11), as well as in non-cancer pathologies such as HHT-1, preeclampsia, and PCOS. Accordingly, disclosed methods and materials can have a wide application across a large number of pathologies, both cancerous and non-cancerous.

The disclosure may be better understood with reference to the following examples.

Example 1

Figure 12:
FIG. 12 illustrates results of staining for the alpha subunit of inhibin (inhibinα) on different tissue types including normal human ovary tissue and tissue obtained from different ovarian cancer subtypes.
Figure 13:
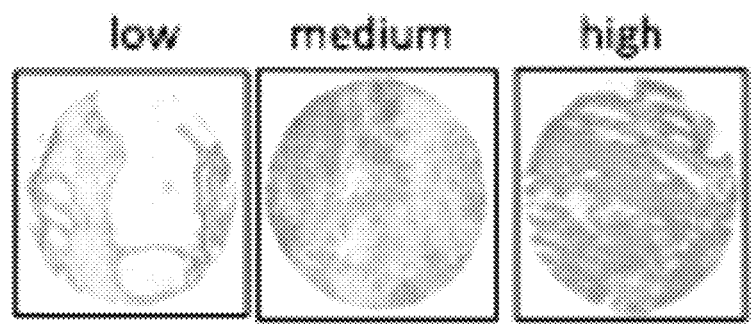
FIG. 13 illustrates typical immunohistochemistry (IHC) responses including low, medium, and high staining response to inhibinα.
Figure 14:
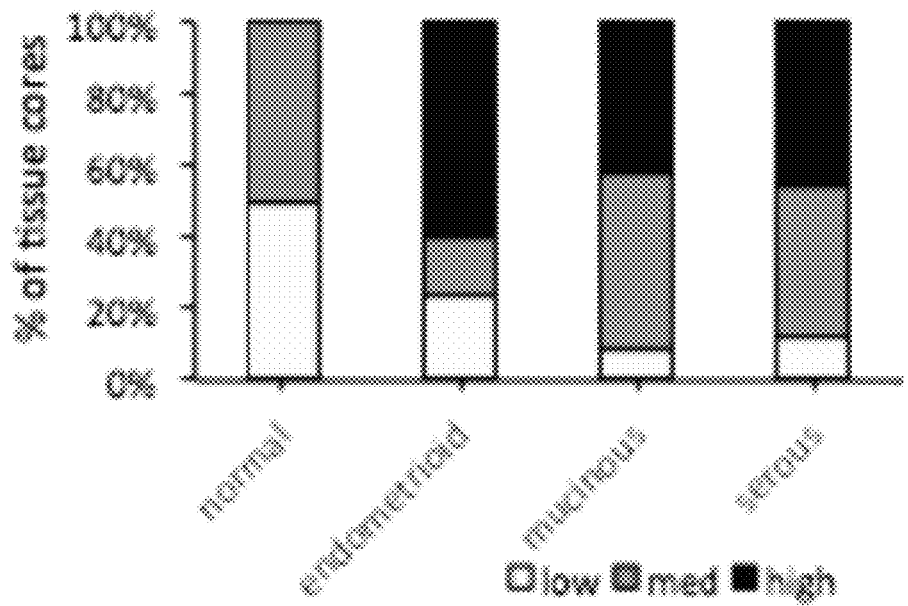
FIG. 14 presents the inhibinα level as a percentage of tissue core for each of the different tissue types.
Figure 15:
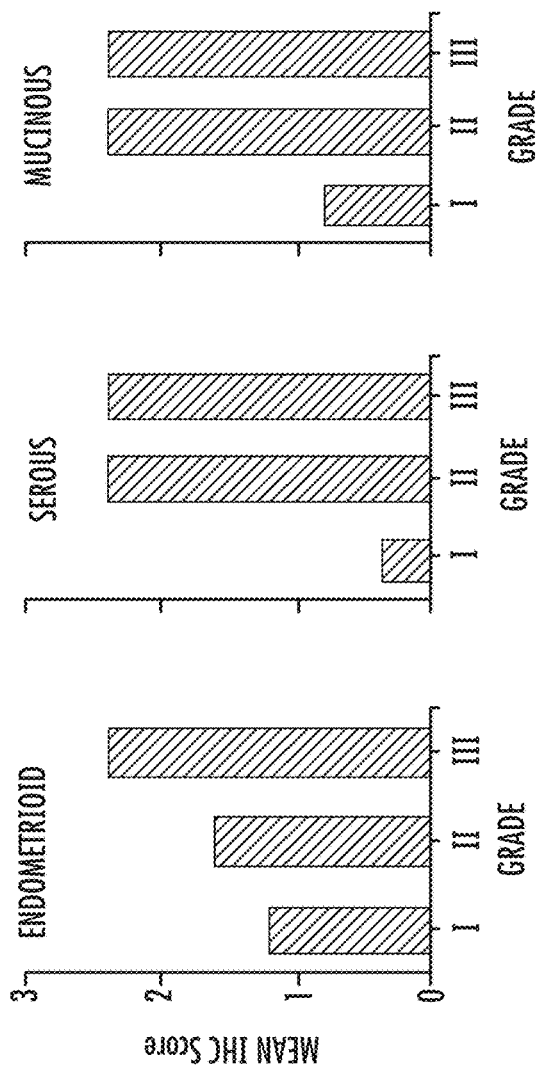
FIG. 15 presents the Inhibinα levels relative to tumor grade (I-III) for each of three different tissue types.

Different tissue types were examined to determine the expression levels of inhibinα. FIG. 12 provides representative images from immunohistochemistry (IHC) of a human ovary cancer tissue microarray (Human Ovary Cancer Tissue Microarray, Protein Biotechnologies) of normal tissue and different ovarian cancer subtypes (endometrial, serous, mucinous) with high inhibinα staining as determined by immunolabeling with anti-Inhibinα antibody and IgG control. As shown, the representative ovarian cores exhibited high staining across subtypes and the specimen of normal ovarian surface epithelium exhibited low Inhibinα staining. Immunoreactivity in the procedure was scored as no, trace or low (1), medium (2), or high (3) staining (FIG. 13). FIG. 14 presents inhibinα levels (as percentage of cores) for each subtype in FIG. 12. FIG. 15 presents the Inhibinα levels relative to tumor grade (I-III) for the tissue type.

Figure 16:
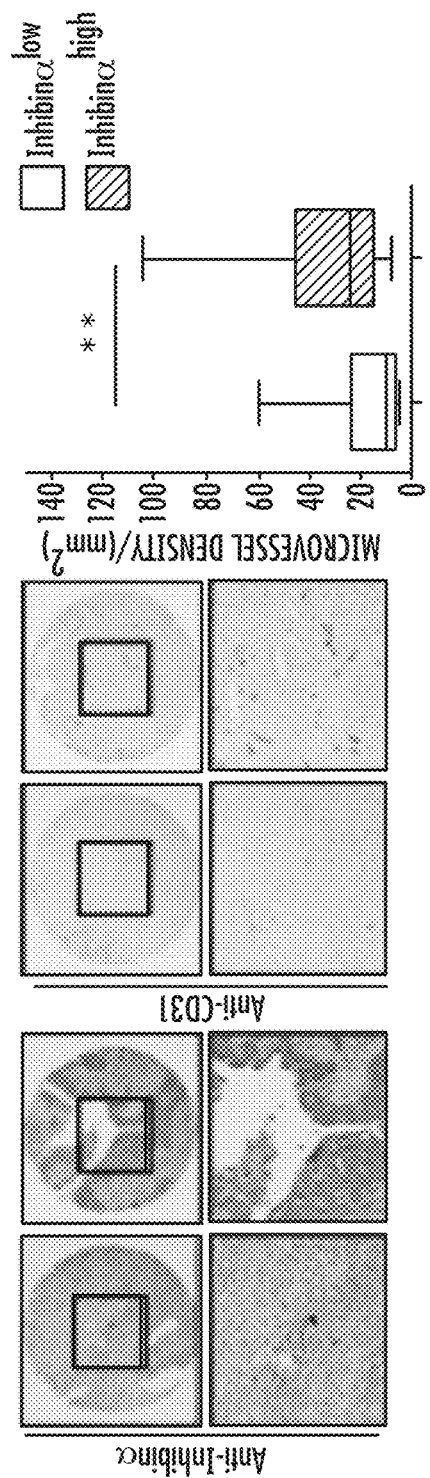
FIG. 16 presents the IHC of the same tissue array immunolabeled with anti-inhibinα (left) or anti-CD31 (middle) antibodies and compares the microvessel density of low and high inhibinα tissue (right).

FIG. 16 presents the IHC of the same tissue array immunolabeled with anti-Inhibinα (left) or anti-CD31 (right) antibodies separately. Representative images of CD31 staining with the corresponding Inhibinα levels in the same cores are shown on the figures and the chart on the right represents quantitation of the microvessel density of the tumor cores with respect to Inhibinα levels quantified (**$P<0.01$).

Results clearly indicate that inhibinα is overexpressed in many cancer cell lines, in accord with previous studies.

Example 2

Figure 17:
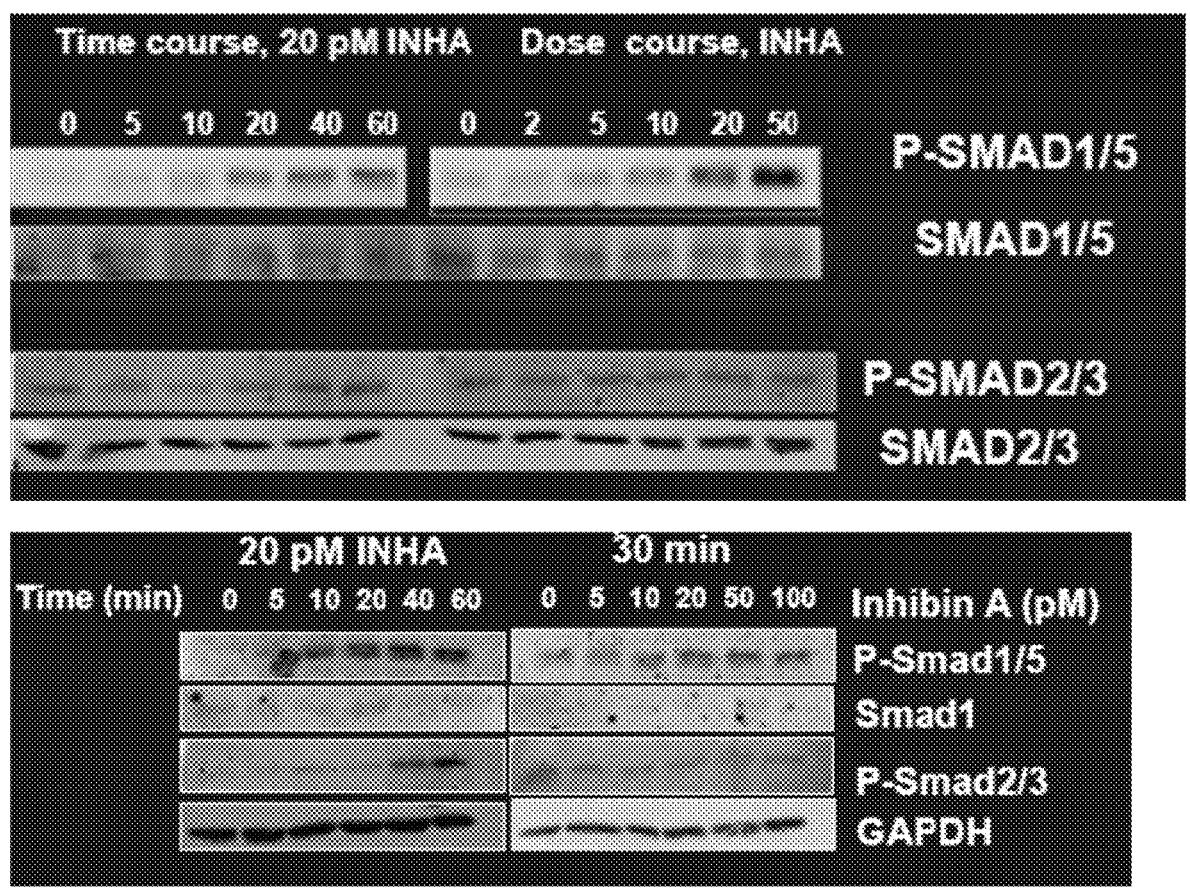
FIG. 17 provides Western blot results for SMAD 1/5 and SMAD 2/3 activation by inhibinα in human microvascular endothelial cells (HMvEC-1).
Figure 18:
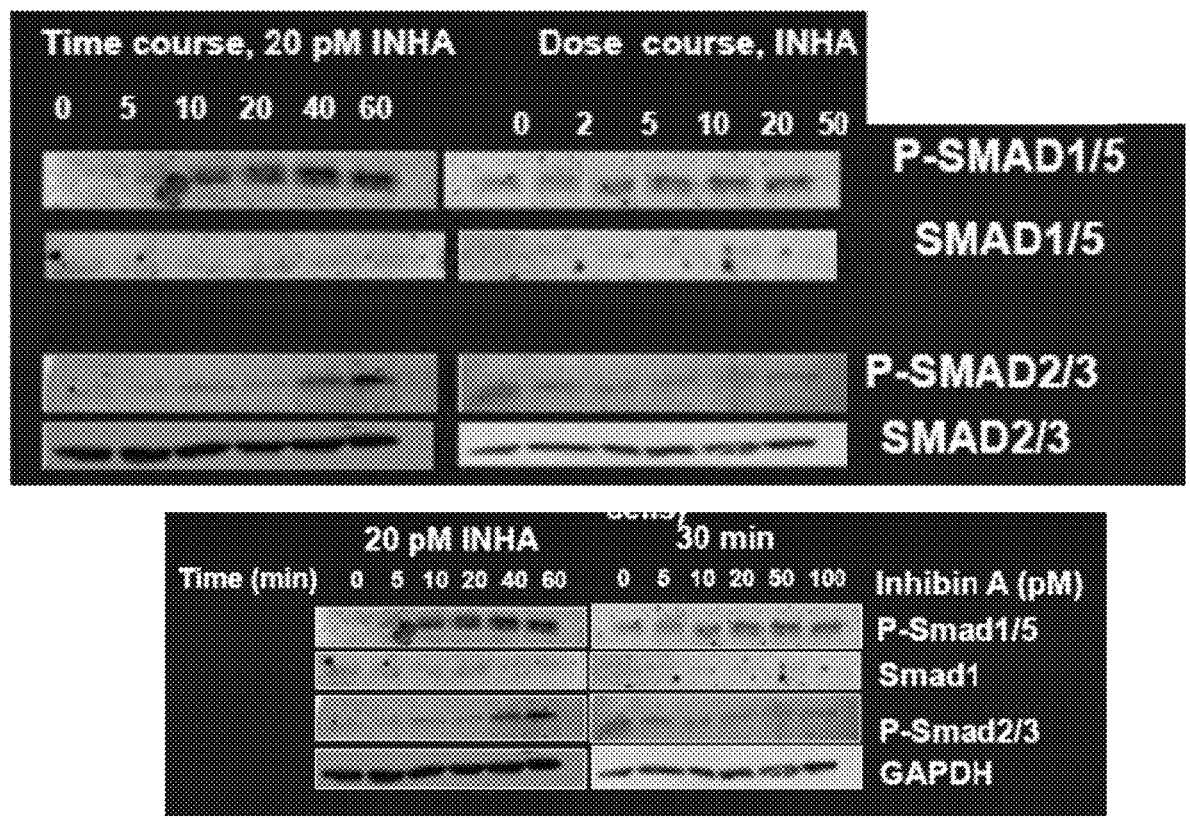
FIG. 18 provides Western blot results for SMAD 1/5 and SMAD 2/3 activation by inhibinα in mouse embryonic endothelial cells (MEEC).
Figure 19:
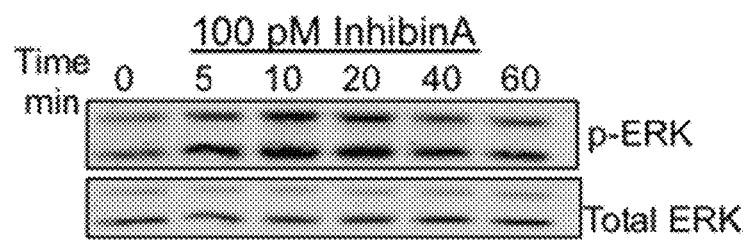
FIG. 19 provides Western blot results for MAPK pathways ERK 1/2 activation by inhibinα in MEEC.
Figure 20:
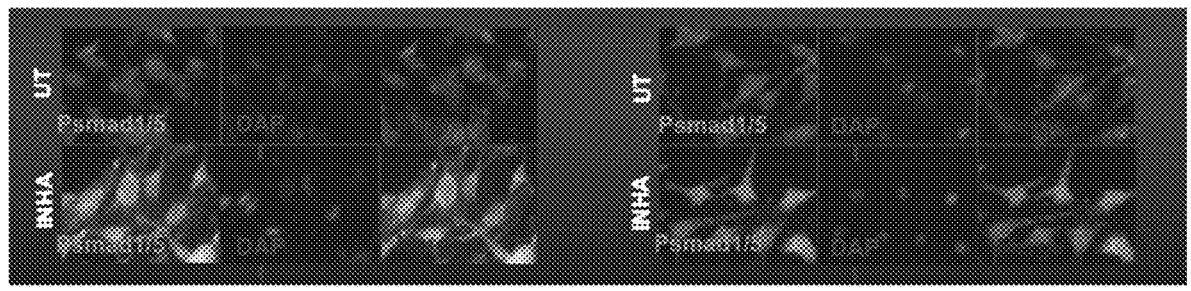
FIG. 20 provides Psmad 1/5 and DAP staining images of endothelial cells following incubation with inhibinα.

Mouse Embryonic endothelial cells (MEEC) and Human Microvascular endothelial cells (HMvEC-1) were examined to determine the effect of inhibinα on SMAD 1/5 activation and on MAPK pathway activation, and specifically, on ERK 1/2 activation. GAPDH or B-actin was used as control. Cells were incubated with 20 pM inhibinα and examined over a time course of 60 minutes and also examined following 30 minute incubation over a dose course from 0 to 100 pM inhibinα. Western blot results are shown of the HMvEC-1 (FIG. 17) and MEEC (FIG. 18). FIG. 19 presents the Western blot time course results following incubation of MEEC with inhibinα for ERK 1/2 activation. FIG. 20 presents image results from staining (Psmad 1/5, DAP, and merged images) for HMvEC-1 cells (left) and MEEC cells (right) following incubation in inhibinα or untreated (UT). Results clearly indicate that inhibinα is a robust activator of SMAD 1/5 and ERK 1/2 in endothelial cells with translocation to the nucleus, but is not equally an activator of SMAD 2/3.

Figure 21:
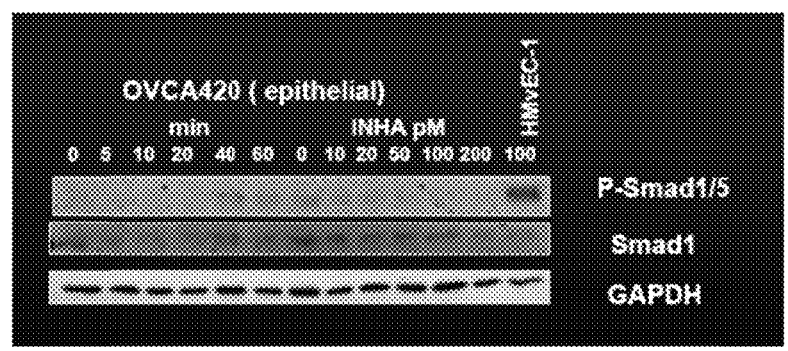
FIG. 21 provides Western blot results for SMAD 1/5 activation by inhibinα in ovarian tumor epithelial cancer cells (HUVEC).

Ovarian carcinoma epithelial cells (OVCA420) were also examined to determine if inhibinα is likewise a SMAD 1/5 activator in these cell types. Western blot results are shown in FIG. 21.

Figure 22:
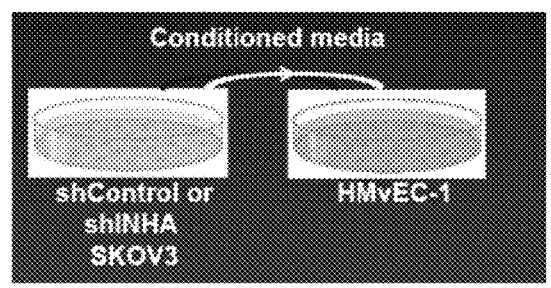
FIG. 22 schematically illustrates a testing protocol described further herein.
Figure 23:
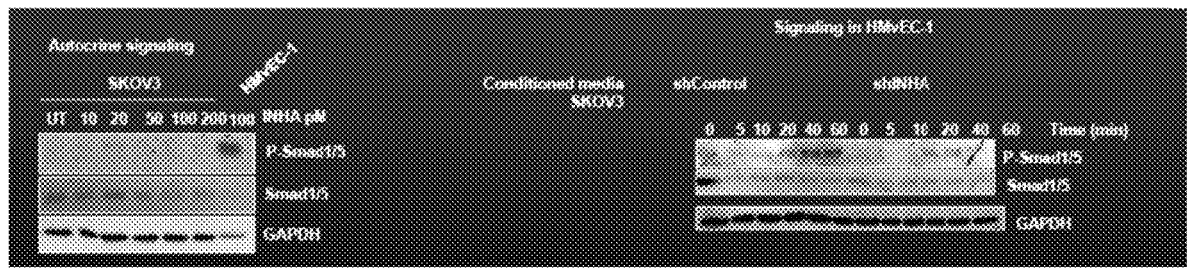
FIG. 23 illustrates Western blot results for HMvEC-1 cells incubated in various conditioned media in determination of inhibinα role in the SMAD 1/5 activation pathway.

To determine if inhibin secreted by ovarian cancer cells activates the SMAD 1/5 pathway in endothelial cells, conditioned media were obtained from stable cell lines that were generated from SKOV3 cells and OVCA420 cells with short hairpin RNA either as a control (with no effective sequence) (shControl), or directed at inhibinα (shINHA), or stable unmodified SKOV3 cells. HMvEC-1 cells were then incubated in one of the conditioned media, as schematically illustrated in FIG. 22. Western blot results are provided in FIG. 23. Results indicate that inhibinα activates the SMAD 1/5 pathway in endothelial cells in a paracrine manner.

Figure 24:
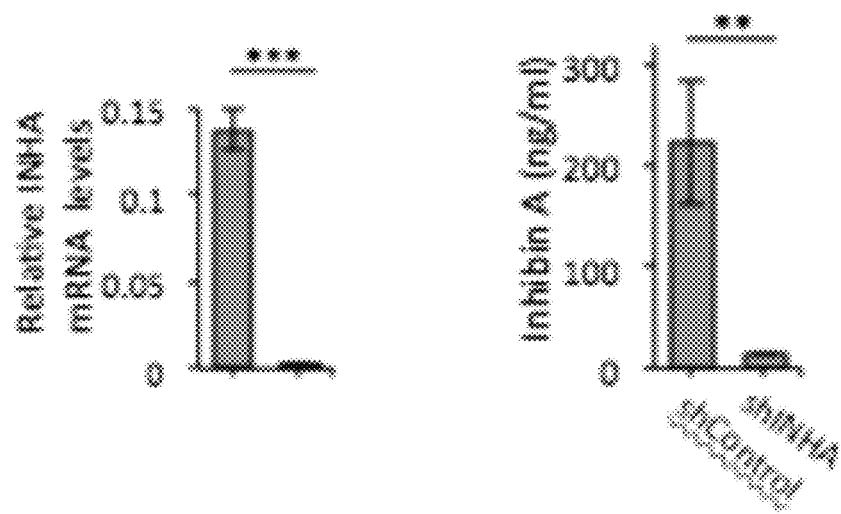
FIG. 24 presents the mRNA levels of inhibinα (left) and total inhibin A levels (right) in stable SKOV3 in control cancer cells (shControl) and cancer cells treated with short hairpin RNA specific for inhibin (shINHA).

FIG. 24 illustrates ELISA results for the mRNA levels of inhibinα (left) and for total inhibin A (right) in stable SKOV3 shControl and shINHA cancer cells.

Figure 25:
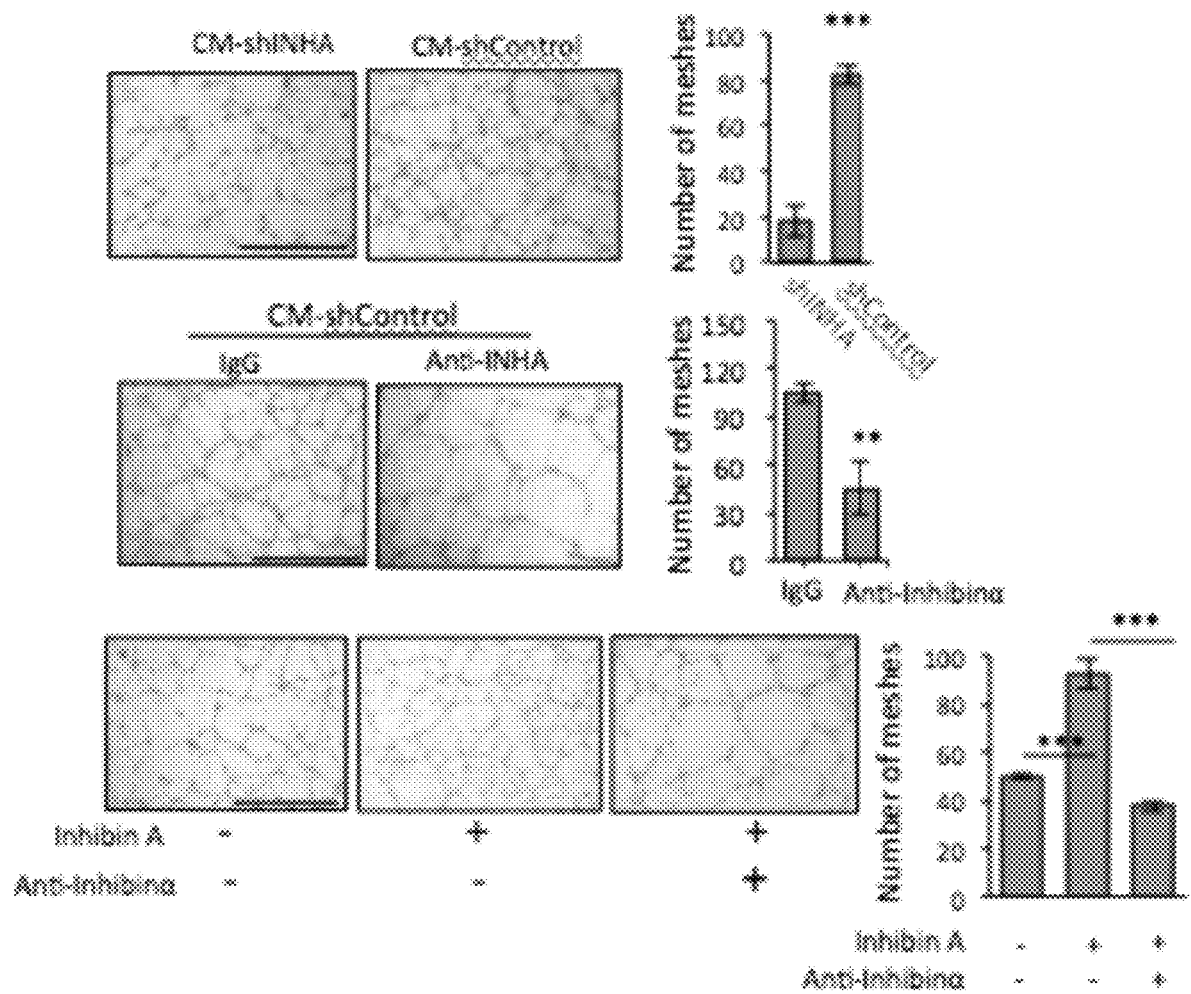
FIG. 25 illustrates the effect of tumor cell secreted inhibina, recombinant Inhibin and anti-inhibinα antibody on angiogenesis.

FIG. 25 illustrates three dimensional capillary sprouting and tube formation of HMvEC-1 cells in the presence of conditioned media (CM) from shControl SKOV3 cancer cells (top), from shINHA SKOV3 cells in the presence of 10 µg/ml anti-inhibinα (middle), and in the presence of IgG control (bottom) treated with 300 pM recombinant inhibinA alone or in the presence of anti-inhibinα antibody (10 µg/ml). The bar graphs represent the average number of meshes quantified and represent duplicate trials. As can be seen, tumor cell-produced Inhibin increased endothelial cell angiogenesis and it can be suppressed by blocking with an anti-Inhibin antibody. The effect of tumor produced-inhibin can be recapitulated by using recombinant Inhibin. (Bar graphs show mean±SEM, *$P<0.001$ and $P<0.01$ (n=3), Student's t-test. Scale Bar=500 µm.)

Figure 26:
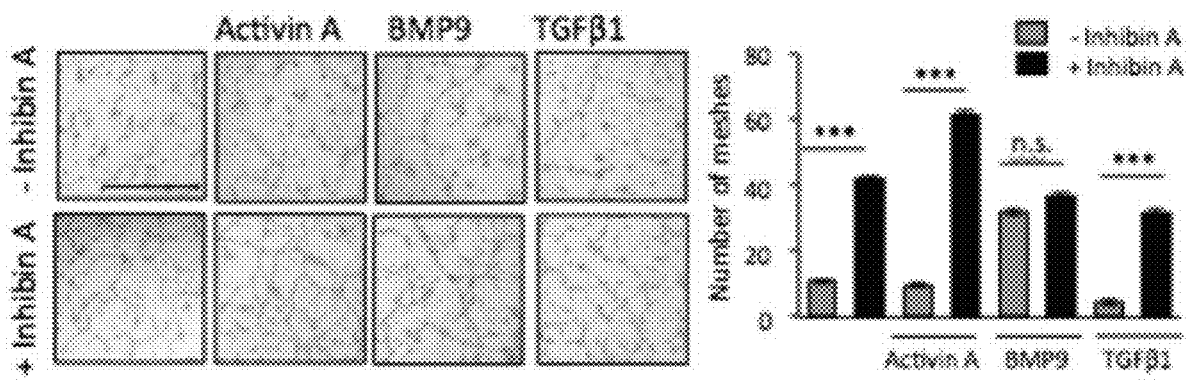
FIG. 26 illustrates angiogenesis in HMvEC-1 cells treated as indicated with TGF-β members (activin A, BMP9, TGFβα) either alone or in the presence of inhibinα.

Other TGF-β members have been reported to have effects on angiogenesis. FIG. 26 illustrates side by side comparison of angiogenesis results for HMvEC-1 cells treated as indicated with other TGF-β members (activin A, BMP9, TGFβα) either alone or in the presence of inhibinα. The robust effect of inhibin on angiogenesis can be seen. The bar graph represents quantitation of number of meshes.

Figure 27:
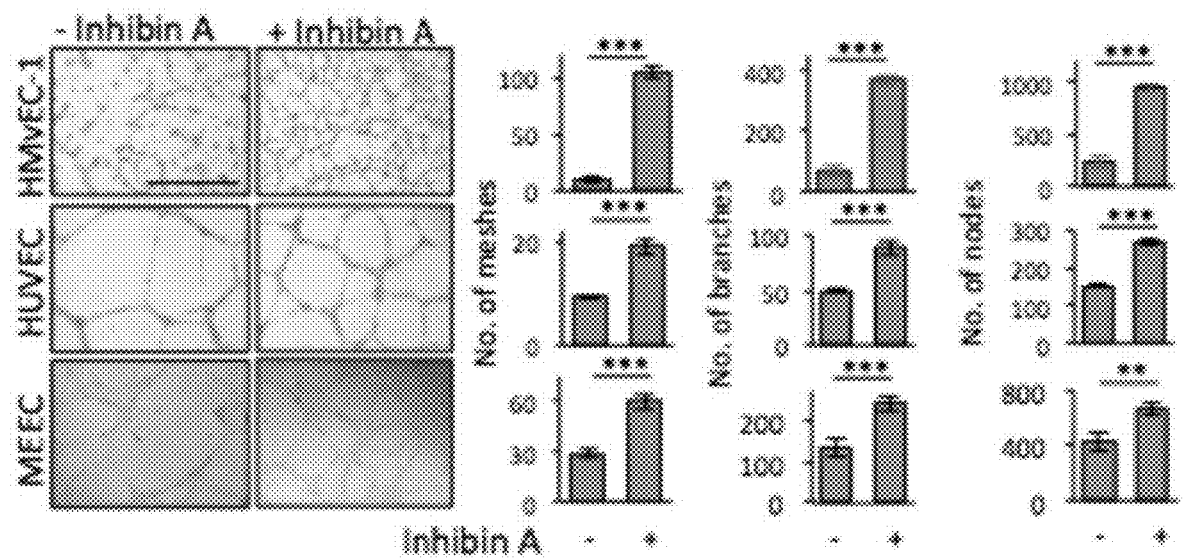
FIG. 27 illustrates angiogenesis in HMvEC-1, HUVEC and MEEC cells upon treatment with 300 pM inhibinα for 16 h.

Use of multiple endothelial cell types (HUVEC, HMvEC, MEEC) illustrates in FIG. 27 capillary sprouting and tube formation of these cell types upon treatment with 300 pM inhibinα for 16 h and the broad effect of inhibin on angiogenesis in different cell types. The graphs represent the number of meshes, branches and nodes quantified. Bar graphs show mean±SEM, *$P<0.001$ and $P<0.01$ (n=3), Student's t-test. Scale Bar=500 µm.

Example 3

Figure 28:
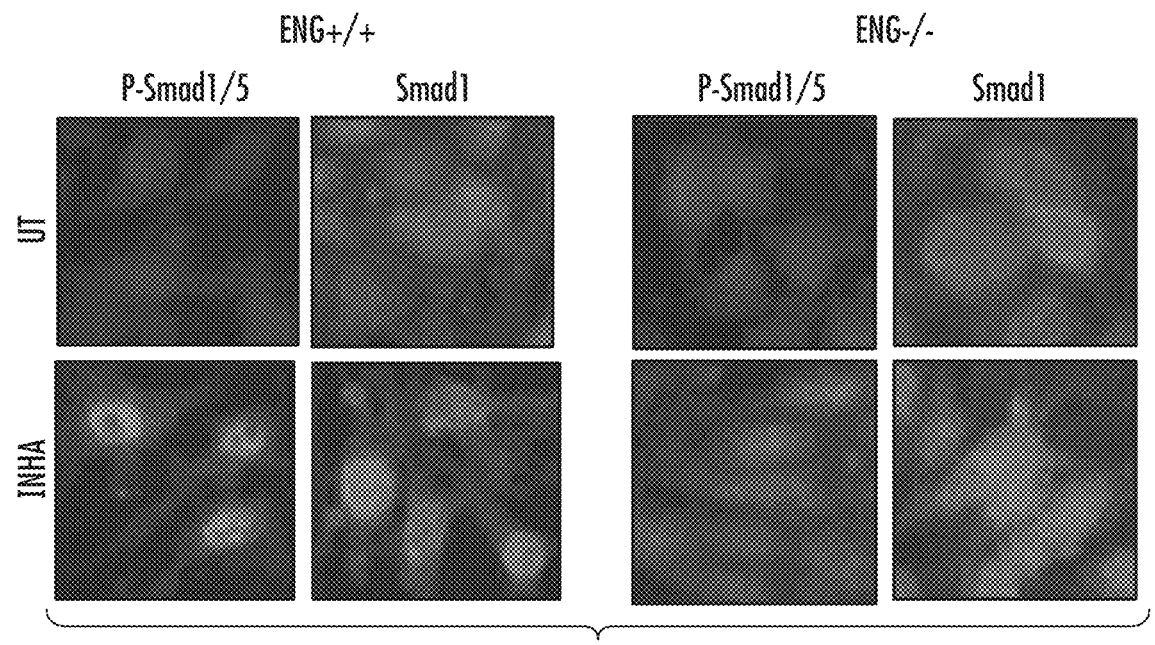
FIG. 28 provides staining images for endothelial cells in determination of endoglin role in inhibin inducement of SMAD 1/5 activation.

Further details of the inhibinα activated SMAD 1/5 pathway were examined. MEEC either positive (MEEC+/+) or negative (MEEC−/−) for endoglin were incubated with 100 pM inhibinα. Staining results are illustrated in FIG. 28.

Figure 29:
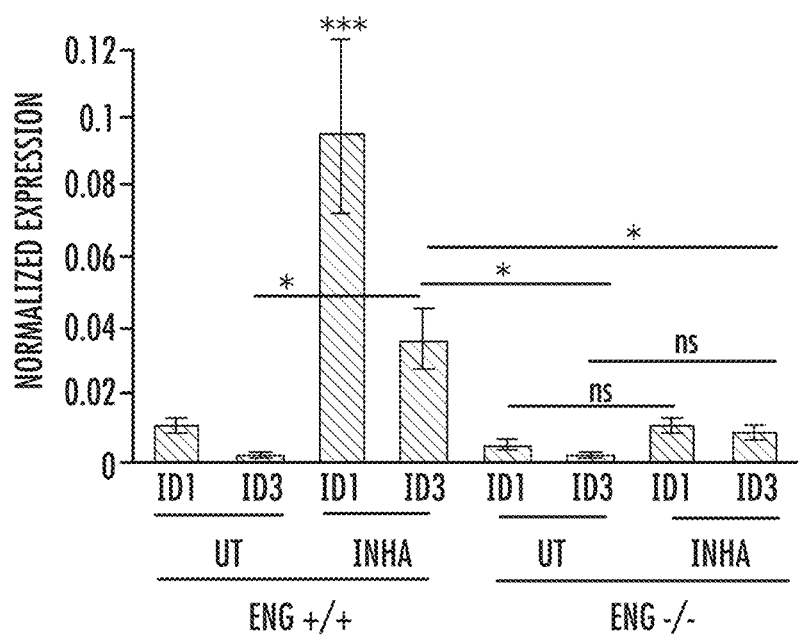
FIG. 29 illustrates the normalized expression of genes ID1, ID3 either in endoglin producing (ENG+/+) or endoglin knockdown (ENG−/−) MEEC cells in response to Inhibin.

FIG. 29 illustrates the normalized expression of genes ID1, ID3 either in endoglin producing (ENG+/+) or endoglin knockdown (ENG−/−) MEEC cells in response to Inhibin.

Figure 30:
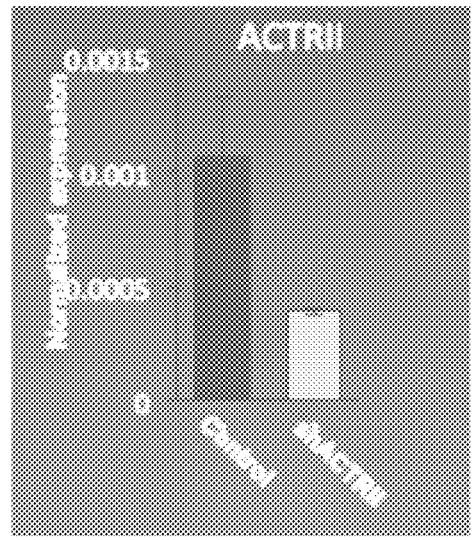
FIG. 30 provides the normalized expression of ACTRII by control cells and cells treated with a short hairpin RNA specific to ACTRII (shACTRII).
Figure 31:
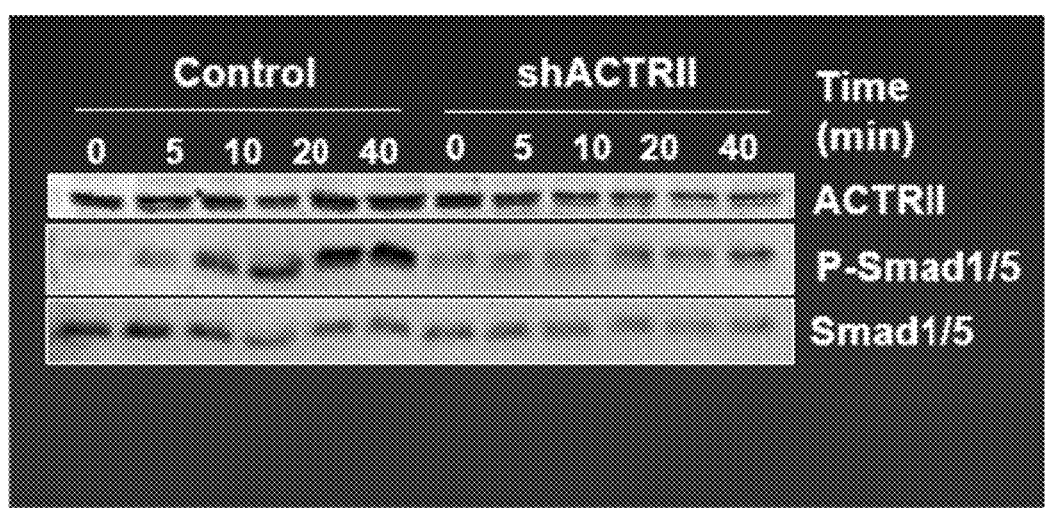
FIG. 31 provides the effect of shACTRII on Inhibin induced SMAd1/5 phosphorylation in HMvEC-1.

The inhibinα activation of the SMAD 1/5 pathway was also examined to determine which receptor type is required. TGF-β receptor serine threonine kinases (Alk1-7) are used by other TGF-β ligands. Testing was done to determine which Type I receptor is utilized by inhibin by using a panel of small molecule inhibitors as a preliminary screen for different Alk's. It was found that inhibition of Alk1/2 but not Alk3/6 or Alk5/4/7 (SB431542) suppressed inhibin induced signaling and angiogenesis. Similarly three type II receptors are expressed in cells: TBRII, ACTRII and BMPRII. Results of the testing (FIG. 30, 31) indicate that inhibinα induced signaling and angiogenesis is dependent on the ACTRII receptor but these results to not rule out TBRII an dBMPRII.

Figure 32:
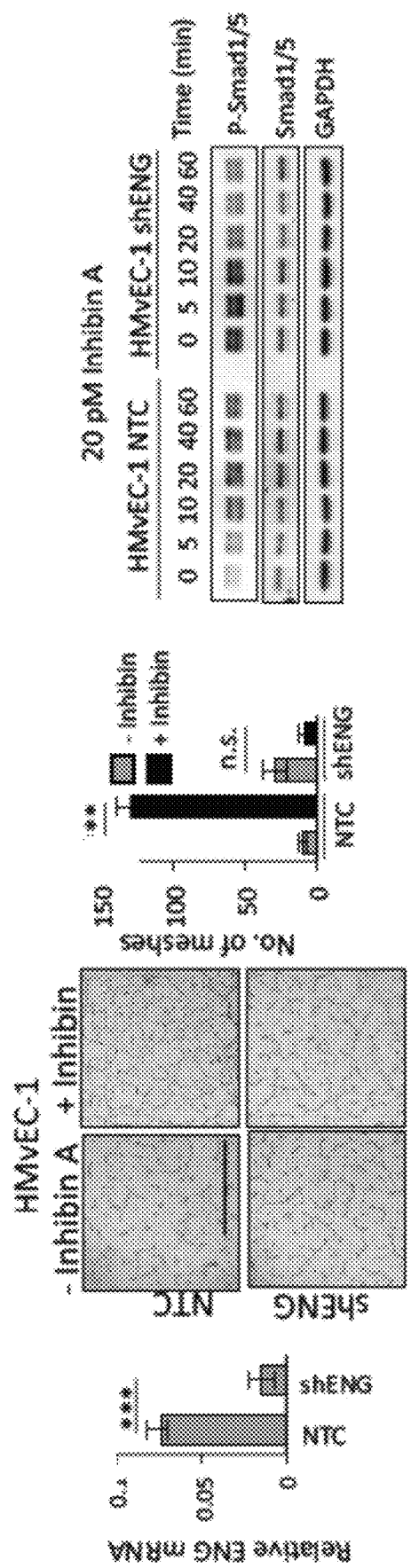
FIG. 32 illustrates effect of shRNA to endoglin in HMvEC-1 cells on Inhibin angiogenesis and SMAD1/5 phosphorylation tested in the presence or absence of recombinant inhibinα.
Figure 33:
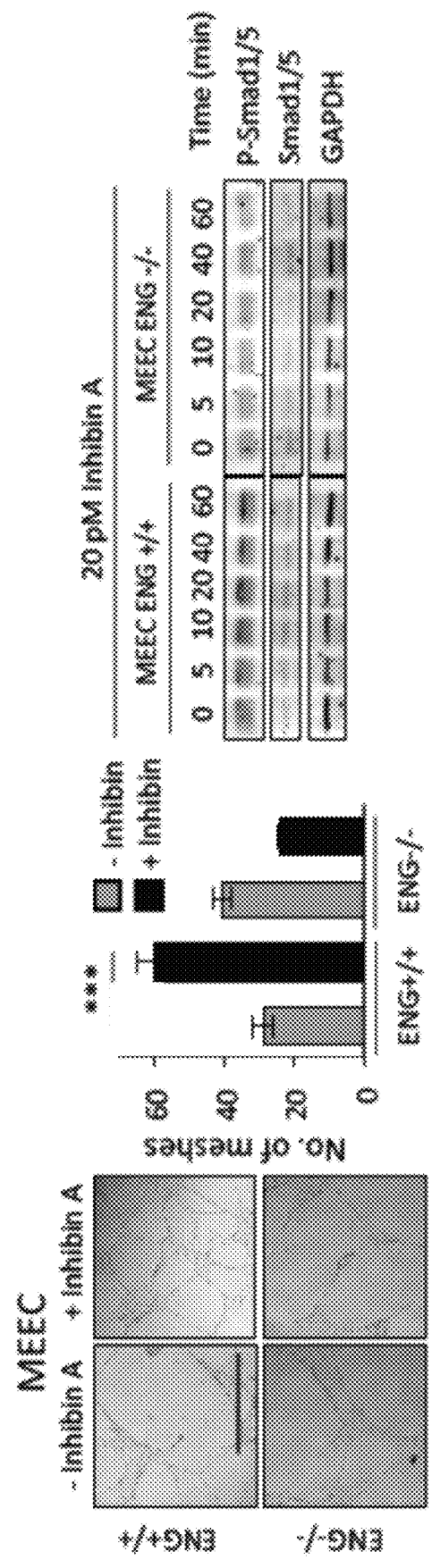
FIG. 33 illustrates angiogenesis in MEEC ENG+/+ cells and endoglin null ENG−/− MEEC's cells in the absence or presence of inhibinα.

Two targets have been determined to be required for inhibina-induced angiogenesis including endoglin (ENG) and ALK1. To verify these targets three approaches were used: shRNA to endoglin to reduce endoglin expression, antibody to endoglin (TRCN105) and mouse embryonic endothelial cells that were knock outs for endoglin. All three approaches indicated that in the absence of endoglin, inhibin does not induce angiogenesis. Similarly shRNA to ALk1 to reduce ALk1 expression indicated that inhibinα induced signaling and angiogenesis is dependent on the ALK1 receptor FIG. 32 illustrates three dimensional capillary sprouting and tube formation of HMvEC-1 cells in the presence or absence of recombinant inhibinα (300 pM) either untreated or pretreated with 100 µg/ml TRC105 for 30 min prior to inhibinα treatment (left, scale bar=500 µm). Average number meshes/field was quantified 16 h after treatment and presented in the bar graph (middle). Minimum of 3 fields were counted and data represent duplicate trials. Western blotting for SMAD1/5 phosphorylation is shown (right) in response to 20 pM inhibinα for up to 60 min FIG. 33 illustrates capillary sprouting and tube formation in MEEC ENG+/+ cells and endoglin null eng−/− in the absence or presence of inhibinα after 16 h. Capillary sprouting and tube formation in the absence or presence of recombinant inhibinα is shown (left, scale bar=500 µm). The graph in the middle illustrates the average number of meshes from a minimum of 3 independent fields and is a representative of duplicate trials. Western blotting for SMAD1/5 phosphorylation in response to 20 pM inhibinα for up to 60 min is shown in the right panel.

Figure 34:
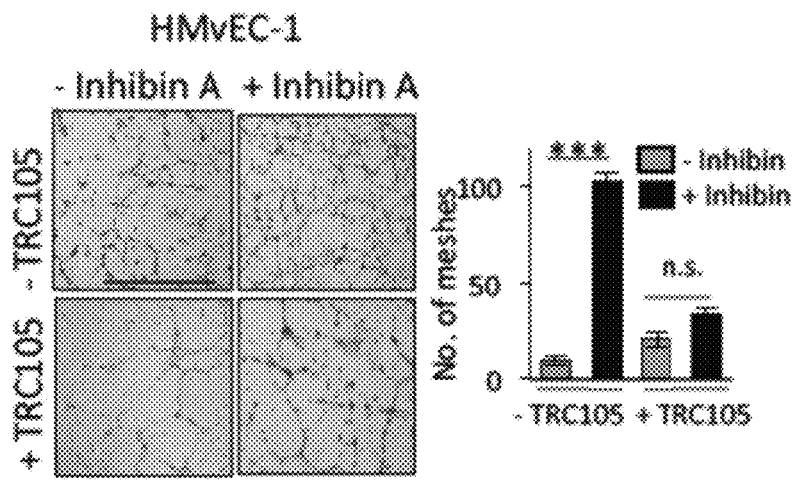
FIG. 34 illustrates angiogenesis in HMvEC-1 cells in response to inhibinα in the absence and presence of 5 µM of TRC105.

FIG. 34 illustrates capillary sprouting and tube formation (left) in HMvEC-1 cells in response to inhibinα in the absence and presence of 5 pM of TRC105 added 30 min prior to treatment with inhibinα. The bar graph on the right represents the number of meshes quantified.

Figure 35:
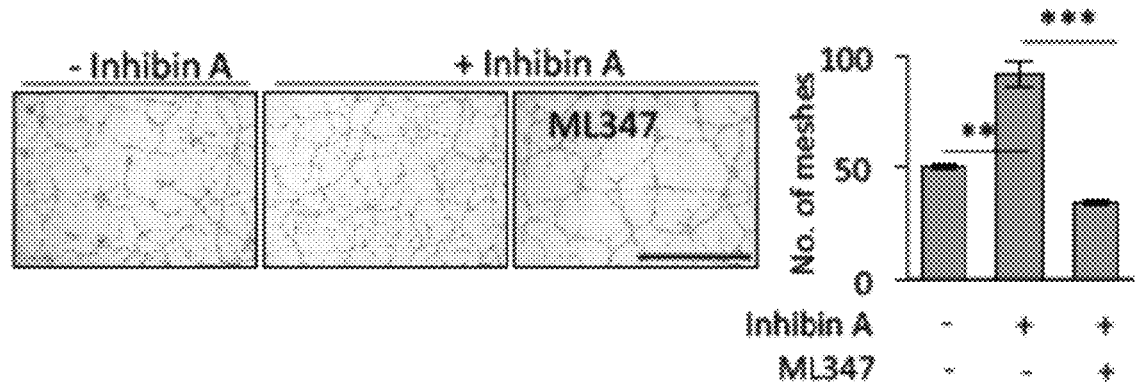
FIG. 35 illustrates angiogenesis in the absence and presence of an Alk1 small molecule inhibitor (ML347) in presence or absence of inhibinα.
Figure 36:
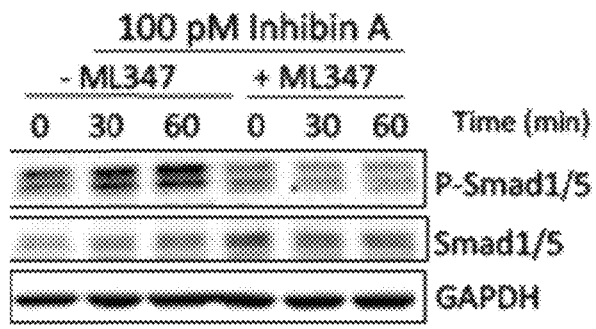
FIG. 36 presents Western blotting results for SMAD1/5 phosphorylation in response to 100 pM inhibinα treatments for up to 60 min in the absence or presence of ML347.

FIG. 35 illustrates capillary sprouting and tube formation in the absence and presence of 5 µM of the ALK1 & 2 small molecule inhibitor ML347 added 30 min prior to treatment with inhibinα. The bar graph on the right illustrates the number of meshes quantified. FIG. 36 presents Western blotting results for SMAD1/5 phosphorylation in response to 100 pM inhibinα treatments for up to 60 min in the absence or presence of ML347.

Figure 37:
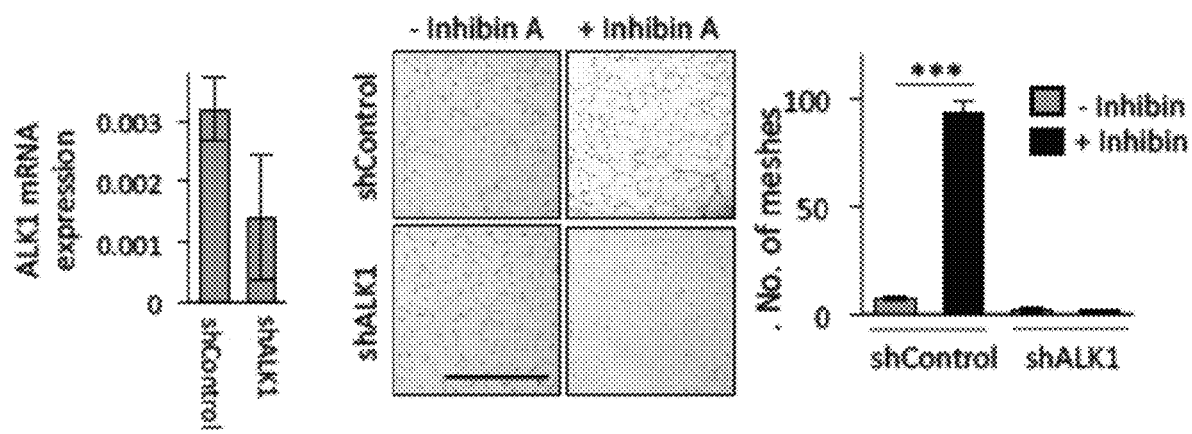
FIG. 37 illustrates angiogenesis in the absence or presence of recombinant inhibinα and in the presence or absence of shRNA to Alk1.
Figure 38:
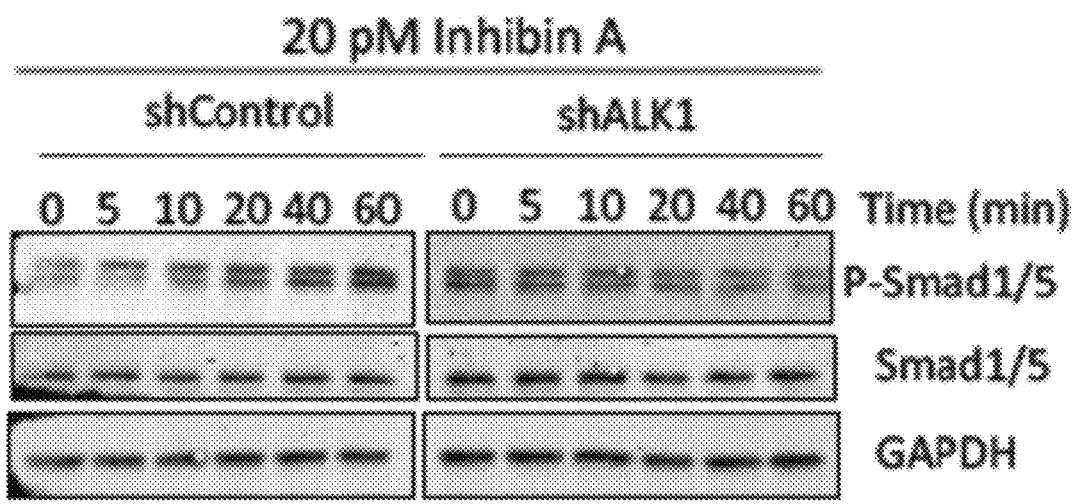
FIG. 38 presents Western blotting results for SMAD1/5 phosphorylation in response to 100 pM inhibinα treatments for up to 60 min following treatment with shRNA to Alk1.

FIG. 37 (left) presents qRT-PCR analysis of ALK1 mRNA expression in HMvEC-1 cells transfected with either control (shControl) or shRNA to ALK1 (shALK1) for 48 hrs. FIG. 37 (middle) illustrates tube formation assays in the absence or presence of recombinant inhibinα. The graph on the right of FIG. 37 represents the number of meshes from a minimum of 3 fields and representative of duplicate trials. FIG. 38 presents Western blotting for SMAD1/5 phosphorylation in response to 20 pM inhibinα treatments for up to 60 min. All graphs represent mean±SEM, *$P<0.001$ and $P<0.01$ (n=3), Student's t-test. Scale Bar=500 µm.

Example 4

Figure 39:
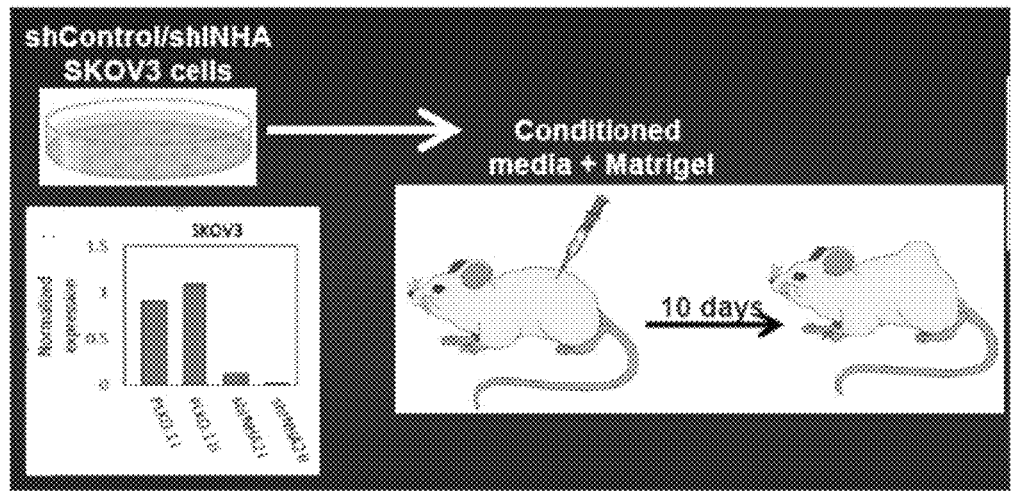
FIG. 39 schematically illustrates an in vivo testing protocol described herein.

In vivo tests were run to determine if paracrine inhibin regulates endothelial angiogenesis in vivo. Briefly, matrigel plug assays were run with shControl/shINHA SCOV 3 conditioned media described above. A schematic of the test procedure is illustrated in FIG. 39.

Figure 40:
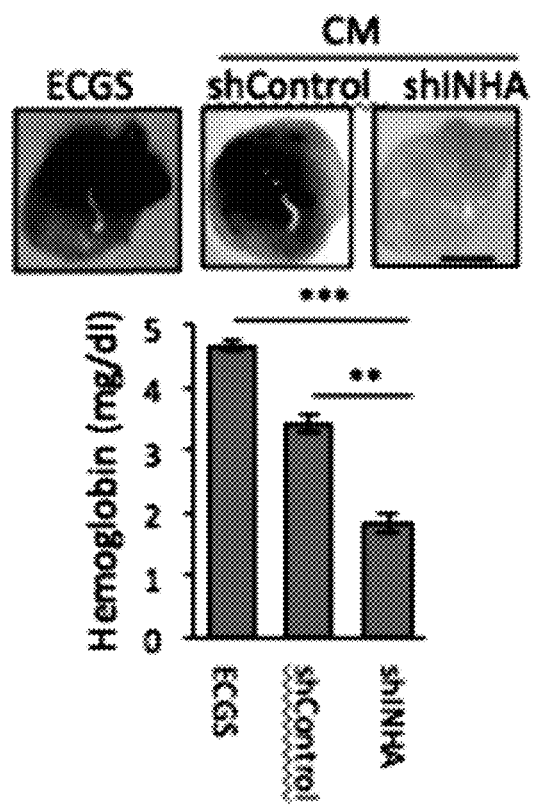
FIG. 40 provides images and hemoglobin quantification of in vivo plugs including matrigel mixed with ECGS, conditioned media from control or inhibina knockdown stable cancer lines.
Figure 41:
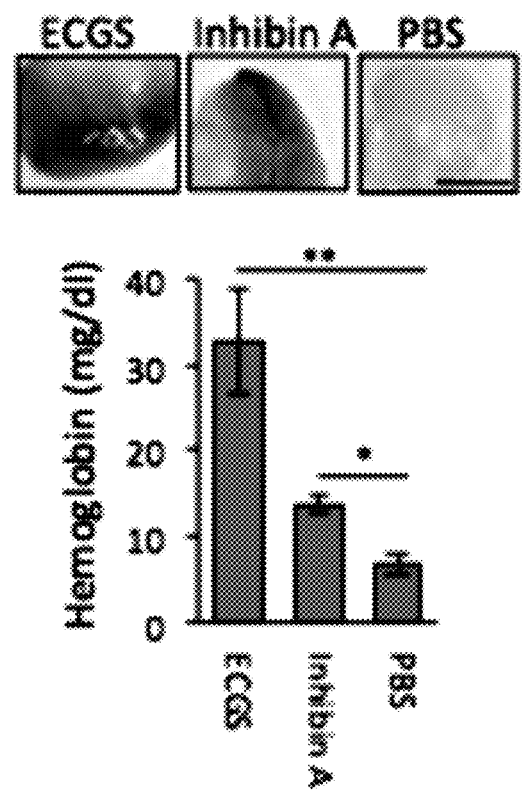
FIG. 41 provides images and hemoglobin quantification of in vivo plugs including matrigel mixed with ECGS, recombinant inhibin and PBS.

FIGS. 40 and 41 are representative images of matrigel plugs (top) and hemoglobin quantification of matrigel plugs (bottom) 12 days post-subcutaneous injection of growth factor reduced matrigel mixed with either 100 ng/ml ECGS (positive control), conditioned media from shControl or shINHA SKOV3 stable cancer in or recombinant inhibinα (100 ng/ml) (FIG. 40) or PBS (negative control) (FIG. 41). Bar graphs represent mean±SEM, (*P<0.001, P<0.01 and *P<0.05, ANOVA with Holm-Sidak post hoc test) (n=3 mice per condition). Scale bar=20 µm.

Figure 42:
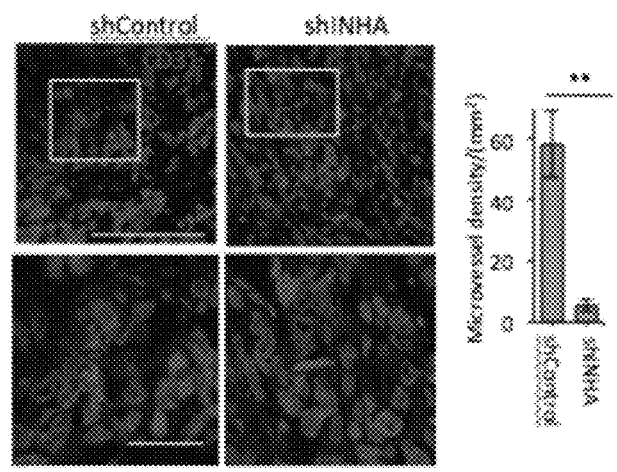
FIG. 42 illustrates the in vivo effects of shRNA to inhibinα on tumor angiogenesis.

FIG. 42 illustrates the effects of shRNA to inhibinα on tumor angiogenesis and includes representative confocal images of IHC of either shControl or shINHA tumors immunolabeled for CD31. Scale bar=1 mm (500 µm in lower panel) (n=5 mice/group) Microvessel density (MVD) was evaluated using CD31 positive endothelial cells in tumor specimens using Image J assisted image analysis. **P<0.01.

Figure 43:
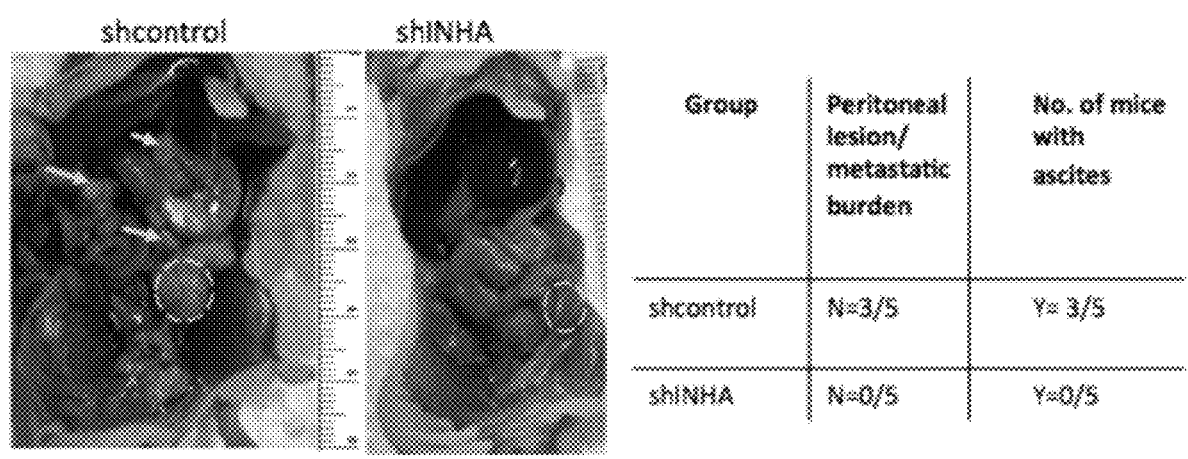
FIG. 43 provides data obtained after 7 weeks of intraperitoneal injections of one million cells, either control or inhibin knockdown cells, in nude mice illustrating effect on peritoneal metastasis.

FIG. 43 provides representative images obtained after 7 weeks of intraperitoneal injections of one million shControl or shINHA SKOV3 cells in nude mice. Ascites, tumor and metastatic burden was qualitatively examined doped circle-ovary (primary site), block arrows—metastatic lesions. Tabulated results from N=5 mice per group is presented on the right. Note the reduced metastatic burden in shINHA mice which have lower inhibin.

Example 5

Figure 44:
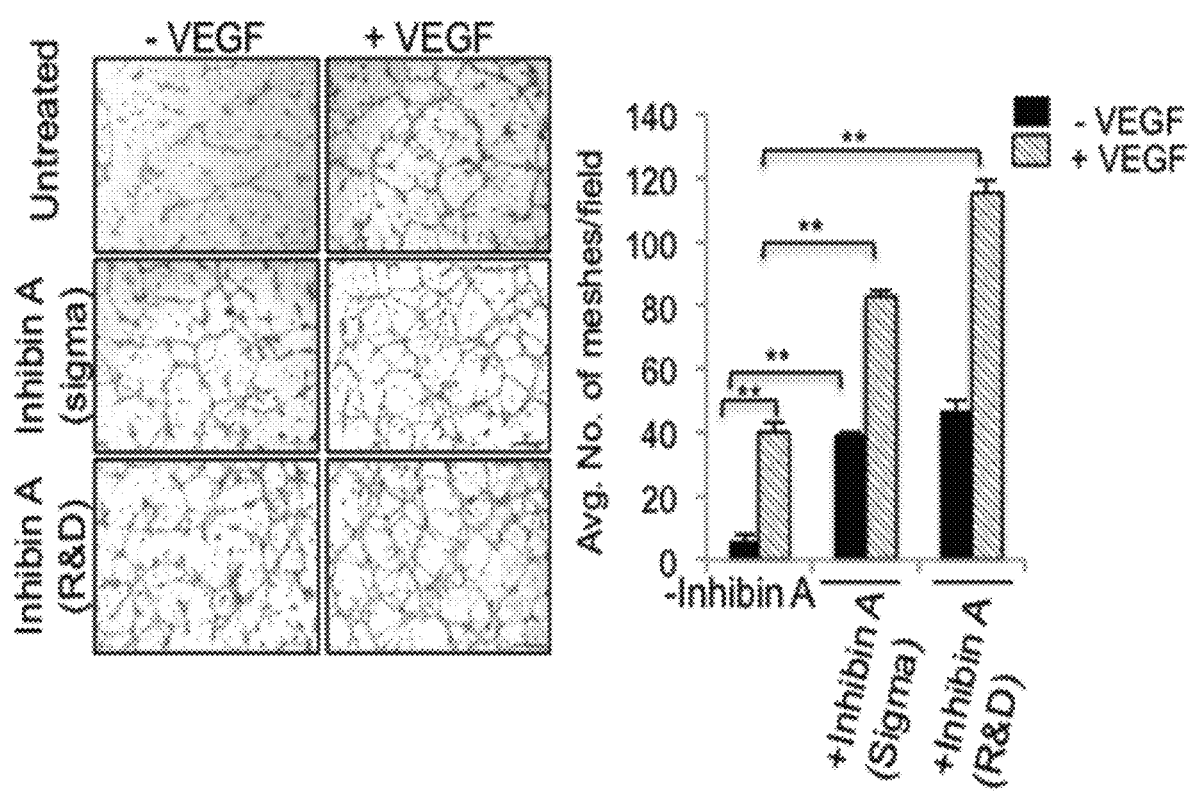
FIG. 44 provides angiogenesis in cells following treatment with VEGF and inhibin, both individually and in combination.

Combination of inhibin with VEGF was examined for synergistic effects. Briefly, matrigel tubulogenesis assay was carried out in HMEC-1 cells either in the presence of equimolar VEGF, inhibin (two independent commercial sources of recombinant Inhibin) or VEGF and inhibin in combination for 16 hrs. Results are shown in FIG. 44. Meshes were quantitated (right) from 3 fields/condition/trial, from 3 independent experiments. **p<0.01. As can be seen, the combination of VEGF with inhibin had a synergistic effect on angiogenesis, This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method comprising:
   contacting an in vitro environment comprising inhibin, media secreted from a cancer cell that expresses the alpha subunit of inhibin, and endothelial cells with a composition comprising a first anti-α-inhibin antibody that specifically binds the alpha subunit of the inhibin; and
   examining the endothelial cells following the contact.

2. The method of claim 1, wherein the cancer cell is an ovarian cancer cell.

3. The method of claim 1, further comprising contacting the in vitro environment with a second antibody that specifically binds an activin receptor-like kinase 1.

4. The method of claim 1, further comprising contacting the in vitro environment with a third antibody that specifically binds endoglin.

5. The method of claim 1, wherein the composition comprises the first anti-α-inhibin antibody at a concentration of from about 0.0001 µM to about 0.5 M.

6. The method of claim 1, wherein the endothelial cells comprise human microvascular endothelial cells.

7. The method of claim 1, wherein the endothelial cells comprise mouse embryonic endothelial cells.

* * * * *